United States Patent
Pollock et al.

(10) Patent No.: US 11,774,536 B2
(45) Date of Patent: Oct. 3, 2023

(54) IMAGING BIOMARKERS BASED ON RATIO BETWEEN DIFFUSION AND PERFUSION

(71) Applicant: OREGON HEALTH & SCIENCE UNIVERSITY, Portland, OR (US)

(72) Inventors: Jeffrey Michael Pollock, Portland, OR (US); Ningcheng Li, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 222 days.

(21) Appl. No.: 17/173,376

(22) Filed: Feb. 11, 2021

(65) Prior Publication Data
US 2021/0255266 A1 Aug. 19, 2021

Related U.S. Application Data

(60) Provisional application No. 62/977,083, filed on Feb. 14, 2020.

(51) Int. Cl.
*G01R 33/00* (2006.01)
*G01R 33/563* (2006.01)
(Continued)

(52) U.S. Cl.
CPC ...... *G01R 33/56366* (2013.01); *A61B 5/0042* (2013.01); *G01R 33/56341* (2013.01); *G16H 30/20* (2018.01)

(58) Field of Classification Search
CPC .............................................. G01R 33/46366
See application file for complete search history.

(56) References Cited

U.S. PATENT DOCUMENTS

8,019,142 B2 * 9/2011 Nowinski ............... A61B 6/032
382/131
9,360,539 B2 * 6/2016 Carroll ............. G01R 33/56366
(Continued)

OTHER PUBLICATIONS

Alsaedi A, et al. Overview and Critical Appraisal of Arterial Spin Labelling Technique in Brain Perfusion Imaging. Contrast Media Mol Imaging. 2018;2018:5360375.
(Continued)

*Primary Examiner* — Joseph M Santos Rodriguez
(74) *Attorney, Agent, or Firm* — Stoel Rives LLP

(57) ABSTRACT

The ratio of arterial spin labeled (ASL) perfusion to diffusion weighted imaging (DWI) is generally homogeneous in the anoxic/hypoxic injury population. Conversely, the ratio is more heterogeneous in the non-anoxic/hypoxic population. By plotting these ratios in a graphical format in the form of an axial color map of the brain—referred to as a normalized diffusion to perfusion (NDP) ratio colormap—it may be determined whether a patient has suffered from an anoxic/hypoxic injury. Thus, the anoxic and non-anoxic injury patients will have, respectively, homogenous and heterogeneous color maps. Anoxic brain injury patients have a global homogeneously positive relationship between qualitative ASL perfusion and diffusion weighted signal such that areas of restricted diffusion show significantly increased ASL perfusion signal, which may be attributable to BBB integrity. The NDP ratio colormap provides an imaging biomarker to differentiate anoxic brain injury from normal controls and to potentially assess BBB integrity.

24 Claims, 24 Drawing Sheets

(51) Int. Cl.
  A61B 5/00    (2006.01)
  G16H 30/20   (2018.01)

(56) References Cited

U.S. PATENT DOCUMENTS

| | | | | |
|---|---|---|---|---|
| 11,229,375 | B2* | 1/2022 | Chen | A61B 5/0042 |
| 2004/0106864 | A1* | 6/2004 | Rose | A61B 5/055 600/410 |
| 2005/0273001 | A1* | 12/2005 | Schmainda | A61B 5/055 600/411 |
| 2007/0086948 | A1* | 4/2007 | Gupte | A61K 49/08 424/9.3 |
| 2007/0167727 | A1* | 7/2007 | Menezes | G06T 7/0012 600/410 |
| 2009/0034812 | A1* | 2/2009 | Nowinski | G06T 19/00 382/131 |
| 2014/0018649 | A1* | 1/2014 | Jespersen | A61B 3/1233 600/363 |
| 2014/0062477 | A1* | 3/2014 | Carroll | G01R 33/4826 324/309 |
| 2015/0247910 | A1* | 9/2015 | Riederer | G01R 33/5619 324/309 |
| 2019/0029557 | A1* | 1/2019 | Chen | A61B 5/7264 |
| 2019/0054194 | A1* | 2/2019 | Yu | G06T 7/168 |
| 2020/0390361 | A1* | 12/2020 | Wang | G01R 33/5618 |

OTHER PUBLICATIONS

Alsop DC, et al. Multisection Cerebral Blood Flow MR Imaging with Continuous Arterial Spin Labeling. Radiology. Aug. 1998;208(2):410-6.
Chao CP, et al. Neonatal Hypoxic-Ischemic Encephalopathy: Multimodality Imaging Findings. RadioGraphics. Oct. 2006;26:S159-72.
De Vis JB, et al. Arterial spin-labelling perfusion MRI and outcome in neonates with hypoxic-ischemic encephalopathy. Eur Radiol. Jan. 6, 2015;25(1):113-21.
De Vis JB, et al. Evaluation of perinatal arterial ischemic stroke using noninvasive arterial spin labeling perfusion MRI. Pediatr Res. Sep. 24, 2013;74(3):307-13.
Deibler AR, et al. Arterial Spin-Labeling in Routine Clinical Practice, Part 1: Technique and Artifacts. Am J Neuroradiol. Aug. 2008;29(7):1228-34.
Deibler AR, et al. Arterial Spin-Labeling in Routine Clinical Practice, Part 2: Hypoperfusion Patterns. Am J Neuroradiol. Aug. 2008;29(7):1235-41.
Deibler AR, et al. Arterial Spin-Labeling in Routine Clinical Practice, Part 3: Hyperperfusion Patterns. Am J Neuroradiol. Sep. 2008;29(8):1428-35.
Dilenge M-E, et al. Topical Review: Long-Term Developmental Outcome of Asphyxiated Term Neonates. J Child Neurol. Nov. 2, 2001;16(11):781-92.
Elster AD. MR contrast enhancement in brainstem and deep cerebral infarction. AJNR Am J Neuroradiol. 1991;12(6):1127-32.
Fugate JE. Anoxic-Ischemic Brain Injury. Neurol Clin. Nov. 2017;35(4):601-611. doi: 10.1016/j.ncl.2017.06.001. PMID: 28962803.
Ghasemi M, et al. Delayed-onset MRI findings in acute chorea related to anoxic brain injury. Clin Imaging. Mar.-Apr. 2018;48:22-25. doi: 10.1016/j.clinimag.2017.10.004. Epub Oct. 5, 2017. PMID: 29028509.
Ghosh A, et al. Comparison of Absolute Apparent Diffusion Coefficient (ADC) Values in ADC Maps Generated Across Different Postprocessing Software: Reproducibility in Endometrial Carcinoma. Am J Roentgenol. Dec. 2017;209(6):1312-20.
Grade M, et al. A neuroradiologist's guide to arterial spin labeling MRI in clinical practice. Neuroradiology. Dec. 2015;57(12):1181-202.
Greisen G. Cerebral blood flow and oxygenation in infants after birth asphyxia. Clinically useful information? Early Hum Dev. Oct. 2014;90(10):703-5.

Heinz ER, et al. Imaging Findings in Neonatal Hypoxia: A Practical Review. Am J Roentgenol. May 2009;192:41-7.
Huang BY, et al. Hypoxic-Ischemic Brain Injury: Imaging Findings from Birth to Adulthood. RadioGraphics. Mar. 2008;28(2):417-39.
Huisman TAGM, et al. Perfusion-weighted magnetic resonance imaging of the brain: techniques and application in children. Eur Radiol. Jan. 1, 2004;14(1):59-72.
Ishaque, M. et al. (2017). White Matter Tract Pathology in Pediatric Anoxic Brain Injury from Drowning. American Journal of Neuroradiology. 38. 10.3174/ajnr.A5097.
Kim SG. Quantification of Relative Cerebral Blood Flow Change by Flow-Sensitive Alternating Inversion Recovery (FAIR) Technique: Application to Functional Mapping. Magn Reson Med. Sep. 1995;34(3):293-301.
Kwong KK, et al. Dynamic magnetic resonance imaging of human brain activity during primary sensory stimulation. Proc Natl Acad Sci. Jun. 15, 1992;89(12):5675-9.
Le Bihan, D, et al., Diffusion MRI at 25: Exploring brain tissue structure and function,NeuroImage, vol. 61, Issue 2, 2012, pp. 324-341, ISSN 1053-8119, https://doi.org/10.1016/j.neuroimage.2011.11.006.
Martinez-Biarge M, et al. Predicting motor outcome and death in term hypoxic-ischemic encephalopathy. Neurology. Jun. 14, 2011;76(24):2055-61.
Massaro AN, et al. Brain Perfusion in Encephalopathic Newborns after Therapeutic Hypothermia. Am J Neuroradiol. Aug. 2013;34(8):1649-55.
McGehee BE, et al. Brain Perfusion Imaging: How Does It Work and What Should I Use? J Magn Reson Imaging. Dec. 2012;36(6):125772.
Paulson OB, et al. Cerebral autoregulation. Cerebrovasc Brain Metab Rev. 1990;2(2):161-92.
Petersen ET, et al. Non-invasive measurement of perfusion: a critical review of arterial spin labelling techniques. Br J Radiol. Aug. 2006;79(944):688-701.
Pienaar R, et al. A quantitative method for correlating observations of decreased apparent diffusion coefficient with elevated cerebral blood perfusion in newborns presenting cerebral ischemic insults. Neuroimage. Nov. 15, 2012,63(3):1510-8.
Pollock JM, et al. Anoxic Injury-Associated Cerebral Hyperperfusion Identified with Arterial Spin-Labeled MR Imaging. Am J Neuroradiol. Aug. 2008;29(7):1302-7.
Proisy M, et al. Changes in brain perfusion in successive arterial spin labeling MRI scans in neonates with hypoxic-schemic encephalopathy. NeuroImage Clin. Jul. 16, 2019;24:101939.
Saliba E, et al. Neuroprotection par hypothermie contrôlée dans l'encéphalopathie hypoxique-ischémique du nouveau-néà terme. Arch Pédiatrie. Sep. 2010;17:S67-77.
Shen Q, et al. Spatiotemporal characteristics of postischemic hyperperfusion with respect to changes in T1, T2, diffusion, angiography, and blood-brain barrier permeability. J Cereb Blood Flow Metab. Oct. 2011;31(10):2076-85.
Sundgreen C, et al. Autoregulation of Cerebral Blood Flow in Patients Resuscitated from Cardiac Arrest. Jan. 2001;32(1):128-32.
Tanaka Y, et al. Arterial spin labeling and dynamic susceptibility contrast CBF MRI in postischemic hyperperfusion, hypercapnia, and after mannitol injection. J Cereb Blood Flow Metab. Jun. 22, 2011;31(6):1403-11.
Volpe JJ. Neonatal Encephalopathy: An Inadequate Term for Hypoxic-Ischemic Encephalopathy. Ann Neurol. Aug. 1, 2012;72(2):156-66.
Walters, F.J.M. Intracranial Pressure and Cerebral Blood Flow. Update in Aneesthesia. Aug. 3, 2019.
Wang J, et al. Pediatric Perfusion MR Imaging Using Arterial Spin Labeling. Neuroimaging Clin N Am. Feb. 2006;16(1):149-67.
Wintermark P, et al. Brain Perfusion in Asphyxiated Newborns Treated with Therapeutic Hypothermia. Am J Neuroradiol. Dec. 2011;32(11):2023-9.
Wintermark P, et al. New Insights in Perinatal Arterial Ischemic Stroke by Assessing Brain Perfusion. Transl Stroke Res. Jun. 10, 2012;3(2):255-62.
Wintermark P. Injury and repair in perinatal brain injury: Insights from non-invasive MR perfusion imaging. Semin Perinatol. Mar. 2015;39(2):124-9.

(56) References Cited

OTHER PUBLICATIONS

Wu Y. Brain Injury in Newborn Babies: We Can't Afford to Get It Wrong. Ann Neurol. Aug. 2012;72(2):151-2. doi: 10.1002/ana. 23673. PMID: 22926847.

* cited by examiner

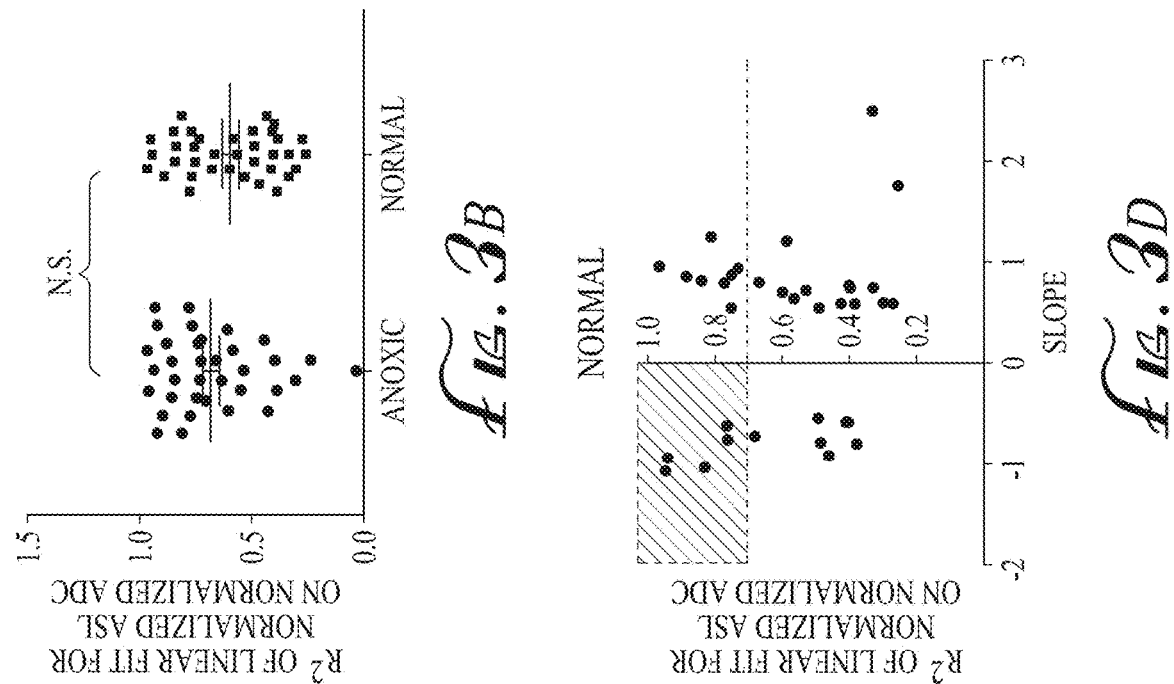
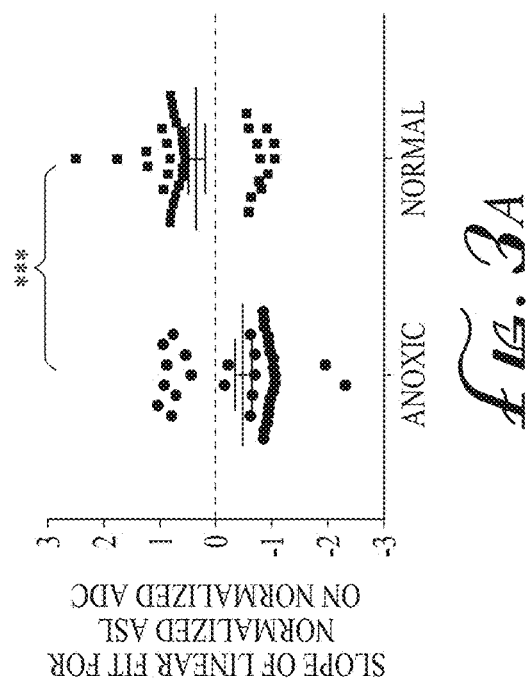
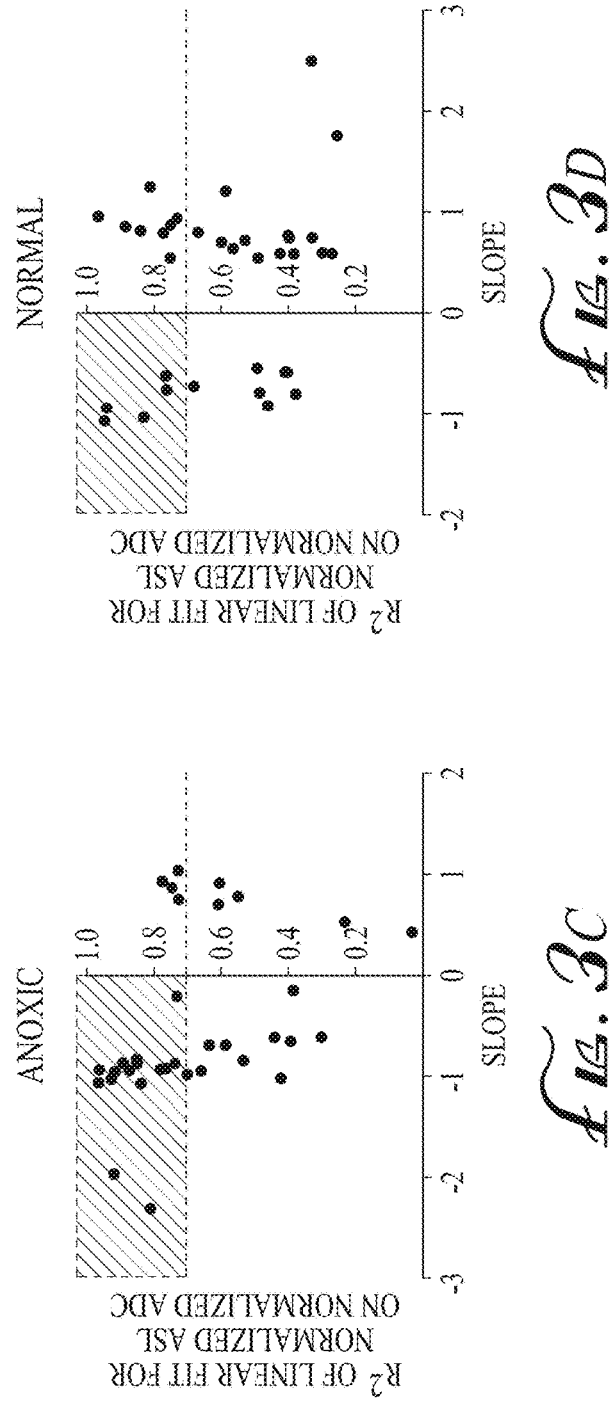
Fig. 3A  Fig. 3B  Fig. 3C  Fig. 3D

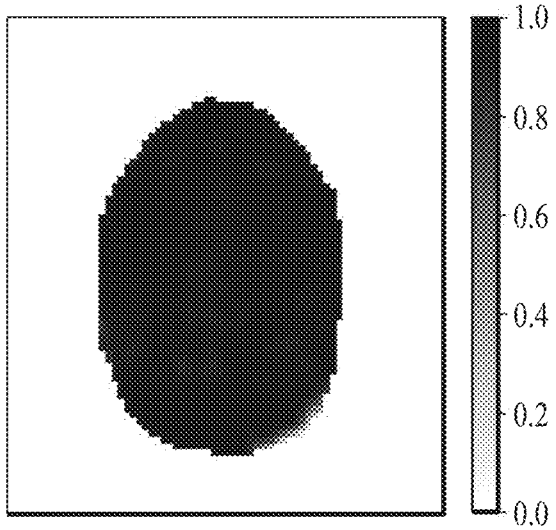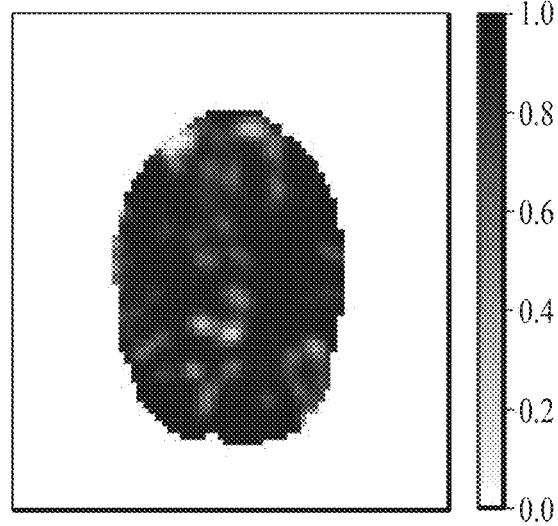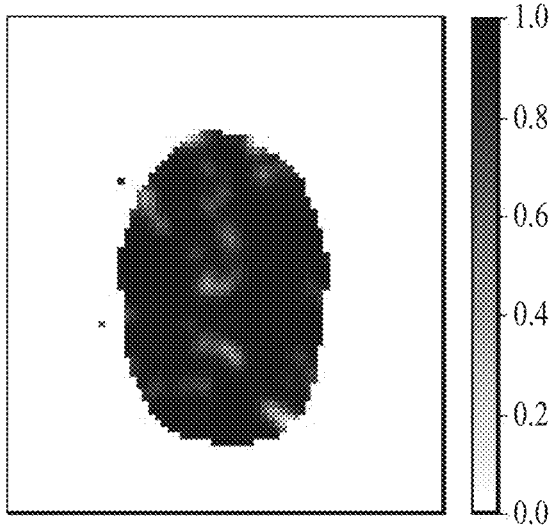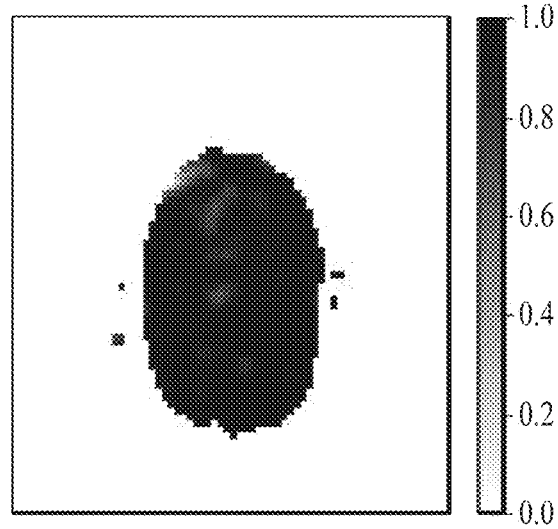
FIG. 7F

IMAGING BIOMARKERS BASED ON RATIO BETWEEN DIFFUSION AND PERFUSION

RELATED APPLICATION

This application claims priority benefit of U.S. Provisional Patent Application No. 62/977,083, filed Feb. 14, 2020, which is hereby incorporated by reference in its entirety.

TECHNICAL FIELD

This disclosure relates generally to magnetic resonance imaging with diffusion restriction and arterial spin labeling and, more particularly, to brain imaging maps.

BACKGROUND INFORMATION

Anoxic brain injury is a result of prolonged hypoxia. Anoxic or hypoxic brain injury has several classic, well-described imaging findings including symmetric diffusion restriction in the basal ganglia and cortex. In the neonatal population, the classic diffusion findings may not be as readily apparent due to the high water content and immature morphology of the brain.

SUMMARY OF THE DISCLOSURE

In one aspect, a method for generating a diffusion to perfusion (DP) ratio brain image, includes receiving magnetic resonance imaging (MRI) data, the MRI data including perfusion and diffusion sequences, and generating the DP ratio brain image based on ratios between co-registered locations of the perfusion and diffusion sequences. The method may also include further includes assigning colors to the DP ratio brain image based on corresponding values of the ratios. The method may also include in which receiving the MRI data includes receiving a digital imaging and communications in medicine (DICOM) file. The method may also include in which the perfusion sequence includes an arterial spin labeling (ASL) sequence. The method may also include in which the diffusion sequence includes a diffusion weighted imaging (DWI) sequence. The method may also include further includes co-registering the perfusion and diffusion sequences on a voxelwise basis. The method may also include further includes resampling one or both the perfusion and diffusion sequences to obtain sequences having equal slice thickness. The method may also include further includes applying a smoothing function to one or both perfusion and diffusion sequences. The method may also include further includes applying a normalization function to one or both perfusion and diffusion sequences optionally to allow comparison among multiple patients. The method may also include further includes generating, based on the DP ratio brain image, an imaging biomarker for differentiating anoxic brain injury from normal controls. The method may also include further includes generating, based on the DP ratio brain image, an imaging biomarker for evaluating physiologic and pathologic changes to the blood brain barrier permeability.

In one aspect, a non-transitory machine-readable storage medium including instructions that when executed by a medical imaging device, cause the medical imaging device to receive magnetic resonance imaging (MRI) data, the MRI data including perfusion and diffusion sequences, and generate the DP ratio brain image based on ratios between co-registered locations of the perfusion and diffusion sequences. The non-transitory machine-readable storage medium may also include in which the instructions further configure the medical imaging device to assign colors to the DP ratio brain image based on corresponding values of the ratios. The non-transitory machine-readable storage medium may also include in which the instructions further configure the medical imaging device to receive a digital imaging and communications in medicine (DICOM) file. The non-transitory machine-readable storage medium may also include in which the perfusion sequence includes an arterial spin label (ASL) sequence. The non-transitory machine-readable storage medium may also include in which the diffusion sequence includes a diffusion weighted image (DWI) sequence. The non-transitory machine-readable storage medium may also include in which the instructions further configure the medical imaging device to co-register the perfusion and diffusion sequences on a voxelwise basis. The non-transitory machine-readable storage medium may also include in which the instructions further configure the medical imaging device to resample one or both the perfusion and diffusion sequences to obtain sequences having equal slice thickness. The non-transitory machine-readable storage medium may also include in which the instructions further configure the medical imaging device to apply a smoothing function to one or both perfusion and diffusion sequences. The non-transitory machine-readable storage medium may also include in which the instructions further configure the medical imaging device to apply a normalization function to one or both perfusion and diffusion sequences optionally to allow comparison among multiple patients. The non-transitory machine-readable storage medium may also include in which the instructions further configure the medical imaging device to generate, based on the DP ratio brain image, an imaging biomarker for differentiating anoxic brain injury from normal controls. The non-transitory machine-readable storage medium may also include where the instructions further configure the medical imaging device to generate, based on the DP ratio brain image, an imaging biomarker for evaluating physiologic and pathologic changes to the blood brain barrier permeability. The non-transitory machine-readable storage medium may also include in which the medical imaging device is an MRI scanner. The non-transitory machine-readable storage medium may also include in which the medical imaging device is a picture archiving and communication system (PACS). Other technical features may be readily apparent to one skilled in the art from the following figures, descriptions, and claims.

Additional aspects and advantages will be apparent from the following detailed description of embodiments, which proceeds with reference to the accompanying drawings.

BRIEF DESCRIPTION OF THE DRAWINGS

FIGS. 2A, 2B, 2C, and 2D are scatterplots of twelve-point ROI linear regression analysis using DWI and ASL sequences, in which FIG. 2A shows patients with anoxic brain injuries demonstrating significantly higher linear regression slopes compared to the normal controls; FIG. 2B shows patients with anoxic brain injuries demonstrating significantly higher linear regression $R^2$s compared to the normal controls; FIG. 2C shows an $R^2$ versus slope scatterplot for patients with anoxic brain injuries identified 34 out of 35 positive cases using a predetermined cutoff of positive slopes and $R^2$ higher than 0.70; and FIG. 2D shows an $R^2$ versus slope scatterplot for normal controls excluded 27 out of 36 negative cases using the same slope and $R^2$ cutoffs.

FIGS. 3A, 3B, 3C, and 3D are scatterplots of twelve-point ROI linear regression analysis using apparent diffusion coefficient (ADC) and ASL sequences, in which FIG. 3A shows patients with anoxic brain injuries demonstrating significantly lower linear regression slopes compared to the normal controls; FIG. 3B shows patients with anoxic brain injuries demonstrating similar linear regression $R^2$s compared to the normal controls; FIG. 3C shows an $R^2$ versus slope scatterplot for patients with anoxic brain injuries identified 17 out of 35 positive cases using a predetermined cutoff of negative slopes and $R^2$ higher than 0.70; and FIG. 3D shows an $R^2$ versus slope scatterplot for normal controls excluded 31 out of 36 negative cases using the same slope and $R^2$ cutoffs.

FIGS. 6A, 6B, 6C, 6D, 6E, 6F, 6G, 6H, and 6I are pictorial views of representative slices of voxel-wise NDP ratio colormap generation, in which FIGS. 6A-6C show anoxic brain injury demonstrated homogeneous NDP ratios throughout the brain; FIGS. 6D-6E show normal control demonstrated heterogeneous NDP ratios throughout the brain; and FIGS. 6G-6I show unilateral anoxic brain injury with one predominately homogeneous (anoxic) right hemisphere and one heterogeneous (non-affected) left hemisphere.

FIGS. 7A, 7B, 7C, 7D, 7E, 7F, 7G, 7H, and 7I are pictorial views akin to those of FIGS. 6A-6I but obtained by reversing the NDP ratio such that perfusion values are in the numerator and diffusion values are in the denominator.

DETAILED DESCRIPTION OF EMBODIMENTS

Figure 1:
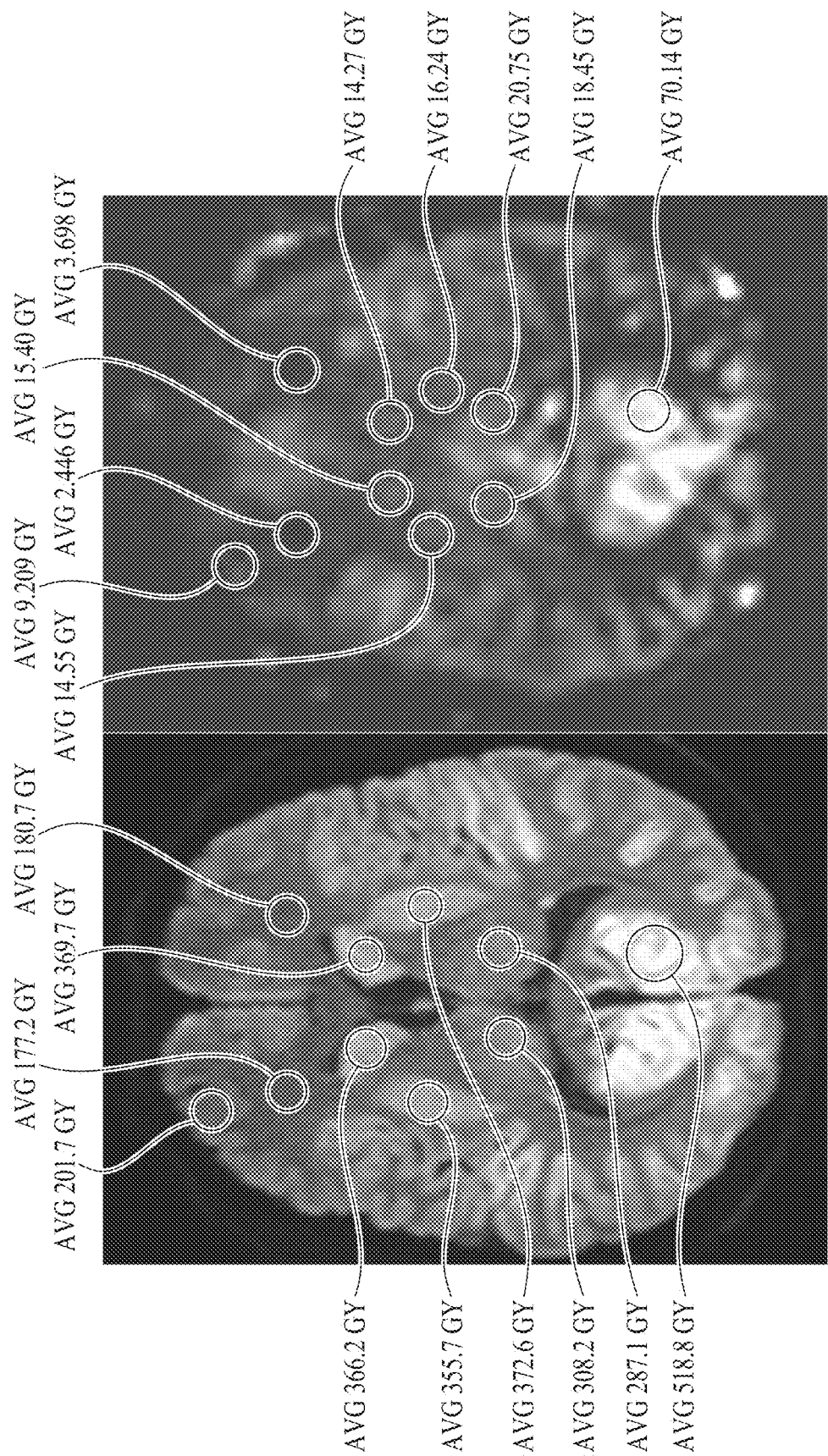
FIG. 1 is an annotated pictorial view of a sample image showing ROI measurements on DWI (left) and ASL (right) at the level of the basal ganglia in a patient who suffered from anoxic brain injury.

Arterial spin labeling (ASL) perfusion is a unique, non-invasive measurement of cerebral blood flow (CBF). ASL perfusion relies on the magnetic tagging of arterial blood water which is then used as a tracer for brain perfusion. The ASL tracer has been assumed to be freely diffusible across the blood brain barrier. However, animal models have shown blood brain barrier (BBB) disruption due to mannitol or stroke increases the ASL perfusion signal relative to the dynamic susceptibility contrast (DSC) perfusion; this suggests that the measured ASL perfusion is dependent on BBB integrity and the ASL signal increases when there is BBB disruption. This BBB dependency has not been shown in humans to date. Additional etiologies including but not limited to tumors and ischemia, which have demonstrated changes in BBB permeability, may also benefit from evaluation with the new metric referred to as a normalized diffusion to perfusion (NDP) ratio.

The ASL sequence has been used to measure perfusion in a variety of pathologies including anoxic brain injury and ischemic strokes. There are a large variety of ASL implementations including but not limited to pulsed arterial spin labeling (PASL), pseudocontinuous arterial spin labeling (PCASL), and continuous arterial spin labeling (CASL). For each variety of ASL there are quantitative and non-quantitative forms. Quantitative forms of ASL have demonstrated a global increase in CBF as well as relative hyper-perfusion in regions with demonstrated injury on conventional MRI in patients with anoxic brain injury. This hyper-perfusion has been theorized to represent flow restoration exceeding the metabolic demands of the injured brain regions with subsequent neurovascular uncoupling, loss of autoregulation, and further brain damage with potential future poor neurological outcomes.

In addition to the quantitative form of ASL, qualitative forms of ASL perfusion are available which display relative differences in CBF. The imaging pattern of anoxic brain injury has not been described with these qualitative forms of ASL perfusion. Nor has there been an effort to quantify the relationship between quantitative or non-quantitative ASL perfusion and diffusion weighted imaging (DWI). DWI information can be derived from traditional diffusion weighted sequences using various B values or the DWI may be acquired by obtaining diffusion tensor imaging (DTI). Apparent Diffusion Coefficient (ADC) may then be generated from the DTI or DWI data.

This disclosure describes non-quantitative ASL perfusion imaging patterns of anoxic brain injury, characterizes the relationship of ASL and DWI, and advances a new metric referred to as a normalized diffusion to perfusion (NDP) ratio by which to differentiate anoxic brain injury from normal controls. Additional etiologies including but not limited to tumors and ischemia, which have demonstrated changes in BBB permeability, may also benefit from evaluation with the new metric referred to as a diffusion to perfusion (DP) ratio or, which sequences are optionally normalized, an NDP.

Also described are example experiments concerning patients diagnosed with anoxic brain injuries from 2002 to 2019. Specifically, the example experiments are based on 35 patients with anoxic brain injuries and 36 normal controls. In the examples, twelve regions of interest (ROIs) are drawn on ASL with coordinate-matched ROIs identified on DWI.

An example linear regression analysis is provided to explain the relationship between ASL perfusion and diffusion signal, i.e., linear regression analysis demonstrates significant positive correlation between ASL and DWI signal. Using a combinatory cutoff of slope>0 and $R^2$>0.70, linear regression using ASL and DWI shows a sensitivity of 0.97 (95% confidence interval (CI): 0.85-1.00) and specificity of 0.75 (95% CI: 0.59-0.86).

Anoxic brain injury is a medical condition with devastating outcomes. Discriminating anoxic from non-anoxic injuries, especially in the neonatal period, is useful for medical management, potential therapeutic hypothermia protocol adjustment, and prognostic estimation. Classic findings of diffusion restriction as well as quantitative hyper-perfusion, especially in the regions of higher metabolic demand such as the basal ganglia and cortex, have been recognized. However, anoxic brain injury patterns on non-quantitative ASL sequences have not been explored. This disclosure characterizes the qualitative ASL perfusion findings in anoxic injury. The present inventors identified the relationship between ASL perfusion and diffusion restriction, which demonstrate a homogeneously positive correlation in patients with anoxic brain injuries such that areas of restricted diffusion showed increased ASL perfusion signal.

In anoxic brain injuries, a homogeneously positive correlation between qualitative ASL perfusion and DWI signal is identified such that areas of increased diffusion signal show increased ASL signal. Exploiting this relationship, an NDP ratio colormap may be a valuable imaging biomarker for diagnosing anoxic brain injury and potentially assessing BBB integrity. Examples of a biomarker that is based on ratios is a numerical representation of the distribution of the DP ratios., range (max-min), mean, median, stan dev., standard errors of the mean, confidence intervals, percentiles, and volatility, any or which may be used for the purpose of making some inference of the brain condition. In general, an NDP ratio colormap demonstrates heterogeneous ratios throughout the brain in normal controls and homogeneous ratios in patients with anoxic brain injuries.

FIG. 1 is an annotated pictorial view of a sample image showing ROI measurements on DWI (left) and ASL (right) at the level of the basal ganglia in a patient who suffered from anoxic brain injury. Review of such information available from 35 patients with anoxic brain injuries demonstrates findings of diffusion restriction (hyperintense on DWI and hypointense on ADC), most commonly in the regions of the basal ganglia, thalamus, and cortex. Rather than global changes in ASL perfusion seen with prior quantitative ASL studies, qualitative ASL perfusion demonstrates regional increases that correlate with the areas of increased DWI signal. It is the inventors' present believe that the relative differences are still apparent and detectable with quantitative techniques, but the global changes may mask these relative differences on typical colormaps which are not adequately scaled to demonstrate these changes.

ROI analyses demonstrate a uniform homogenously positive relationship between the ASL perfusion signal and the DWI signal in the selected regions among patients with anoxic brain injuries (see generally, FIGS. 2A-2D). This relationship held true not only in the more commonly described basal ganglia regions, but also the cortical grey matter and white matter regions. Analysis of the ADC signal revealed a similar relationship, consistent with results demonstrating significant correlation between decreased ADC and elevated ASL-CBP signals; however, the diagnostic performance was different (see generally, FIGS. 3A-3D), likely due to higher susceptibility to volume average artifacts from the surrounding CSF or intrinsic properties yet to be delineated causing higher ASL-CBP elevation than the corresponding ADC abnormality.

The explanation for the observed perfusion signal observations in the anoxic population may be due to several factors. The homogenously positive relationship between ASL and DWI may be related to changes in the blood brain barrier (BBB) permeability. Some researchers previously showed that the ASL perfusion sequence tends to overestimate CBF in ischemic stroke in an animal model. Unilateral injection of mannitol in normal animals, which increased the permeability of the BBB also increased the ASL signal. Assuming the magnetically tagged water molecules are freely diffusible across the BBB, they postulated that ischemic stroke injuries, with subsequent disruption of the BBB, allowed increased extravasation of water molecules implying that ASL perfusion signal is dependent on BBB integrity.

Based on the results of the animal studies and current data, it is the inventors' present belief that in an anoxic injury, there is both a global and regional disruption of the BBB, especially in the regions of higher metabolic demands, leading to regional increases in ASL signal that correlate with the areas of greatest diffusion restriction. Non-dependence of the positive relationship between ASL and DWI signal on the time interval from injury to imaging (see FIGS. 4A and 4B) suggests the BBB injury is present and enduring up to 14 days (range: 0-14 days after reported inciting event). This BBB disruption is normally seen on gadolinium contrast enhanced MRI two to three days after ischemic injury and may persist for months; however, it is conceivable that the BBB injury occurs earlier than two to three days and it is only after two to three days that the BBB disruption is great enough for the gadolinium particles to cross the BBB. Gd-DOTA, a commonly used chelated gadolinium contrast media, has a size of two nm, compared to 0.275 nm of a water molecule. ASL utilizes the protons within the blood water making the ASL sequence much more sensitive to early changes in the BBB pore size. Although there is not a significantly non-zero slope, positive trends of both the linear regression slope and $R^2$ over interval to imaging were observed (see FIGS. 4A and 4B). This may suggest that the repair of the BBB is gradual and lags behind the pseudonormalization of the diffusion signals, a phenomenon where diffusion-weighted imaging improves and appears normal by the end of the first week. Gradually decreasing metabolic demands due to delayed cell death during the energy failure component of the reperfusion phase with persistent BBB disruption could theoretically have contributed to a similar relationship. Further research with animal models and survival studies could delineate the underlying physiologic response and to evaluate the effects of BBB disruption in humans and the recovery of BBB integrity.

Among normal controls, significantly lower $R^2$ and lower slopes of the linear regression models implied underlying heterogeneity of the relationship between the ASL perfusion and the DWI signal. Analyses of the ADC also demonstrate similar results. The lack of a homogeneous relationship is likely secondary to a much lower signal-to-noise ratio among the intracranial structures in normal controls. Small variability in metabolic demand, regional perfusion, BBB permeability, and the inherent delay of the auto-regulation feedback loop may have contributed to the demonstrated heterogeneities.

Figure 6A:
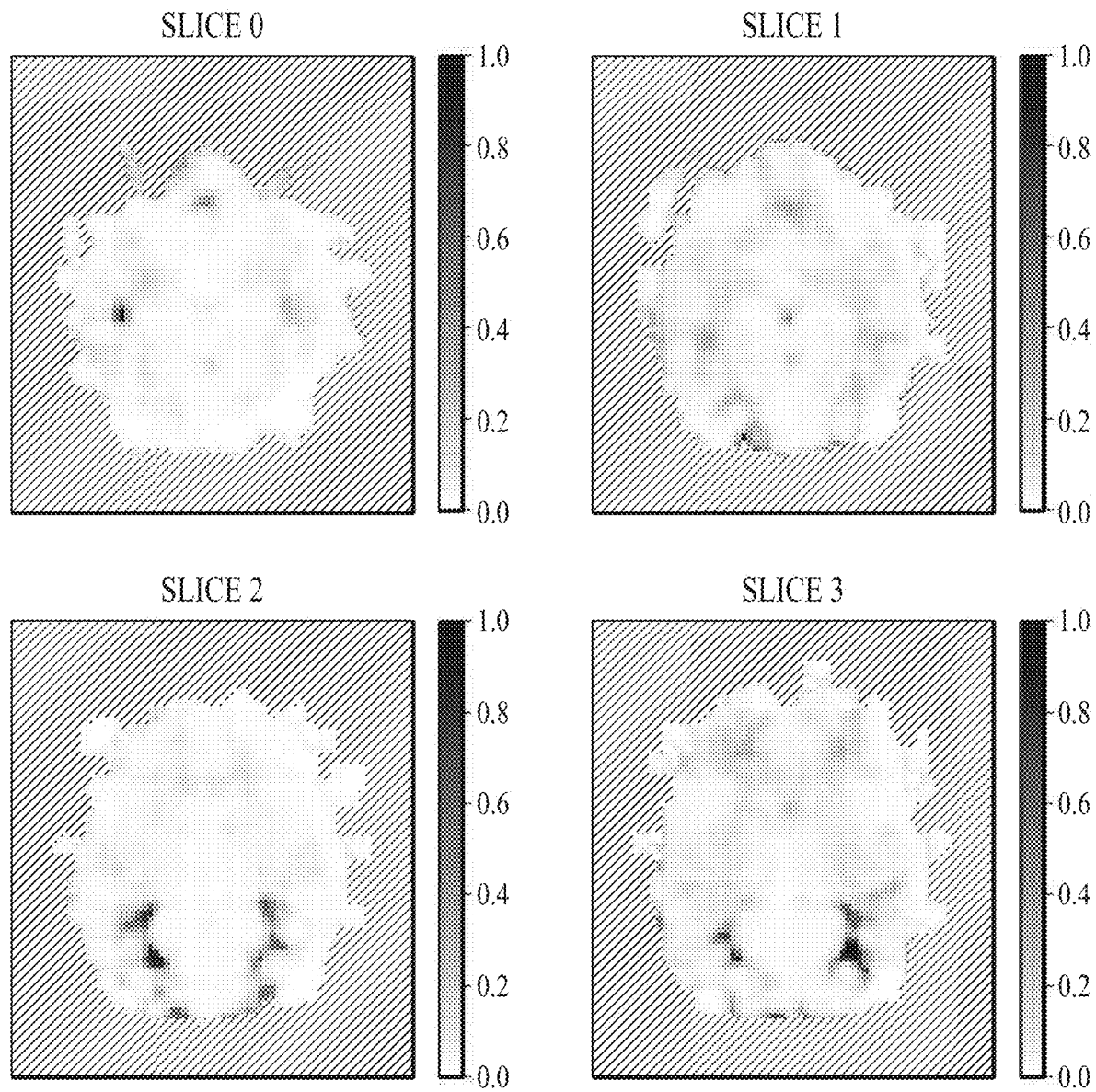
Figure 6B:
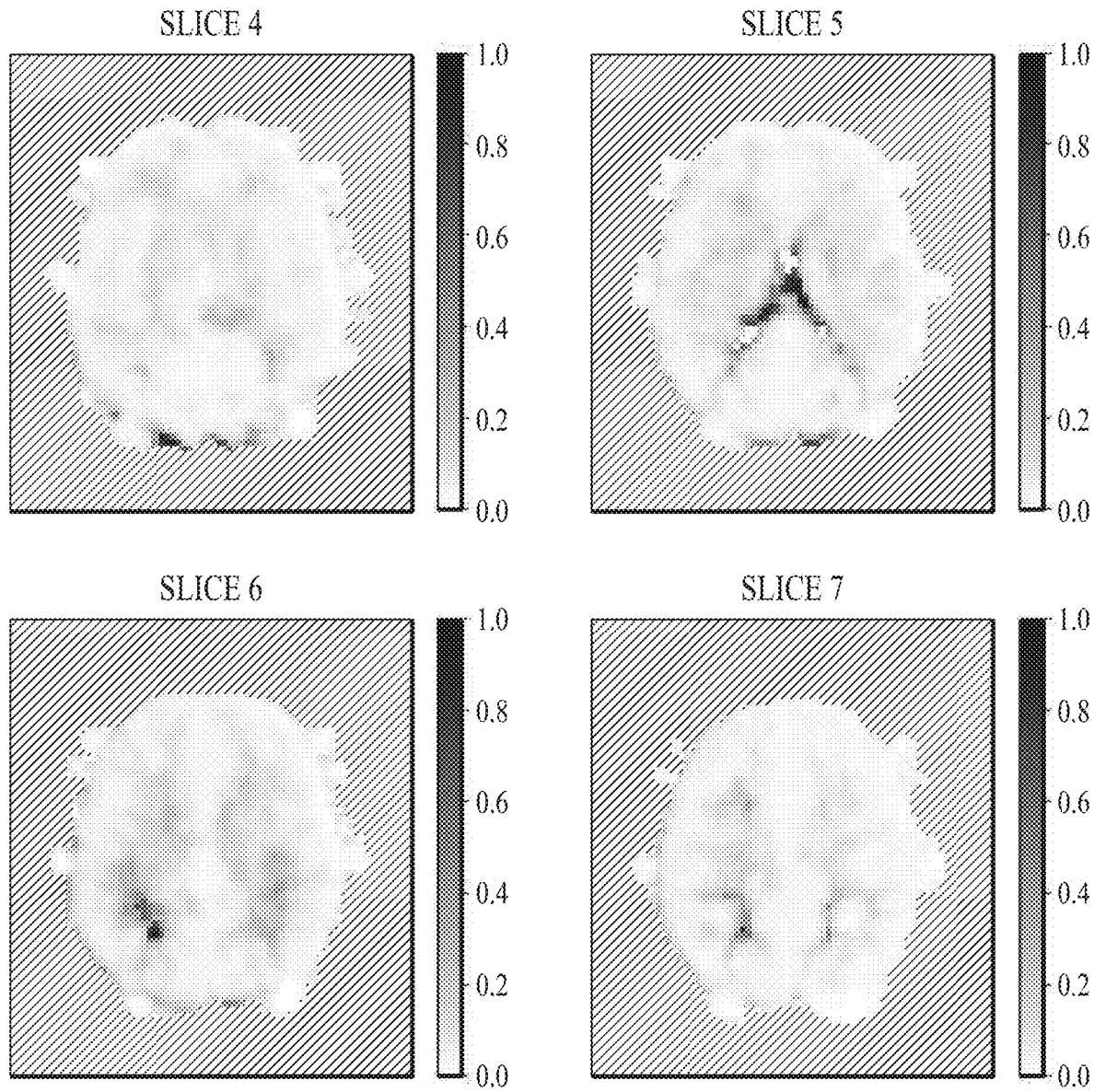
Figure 6C:
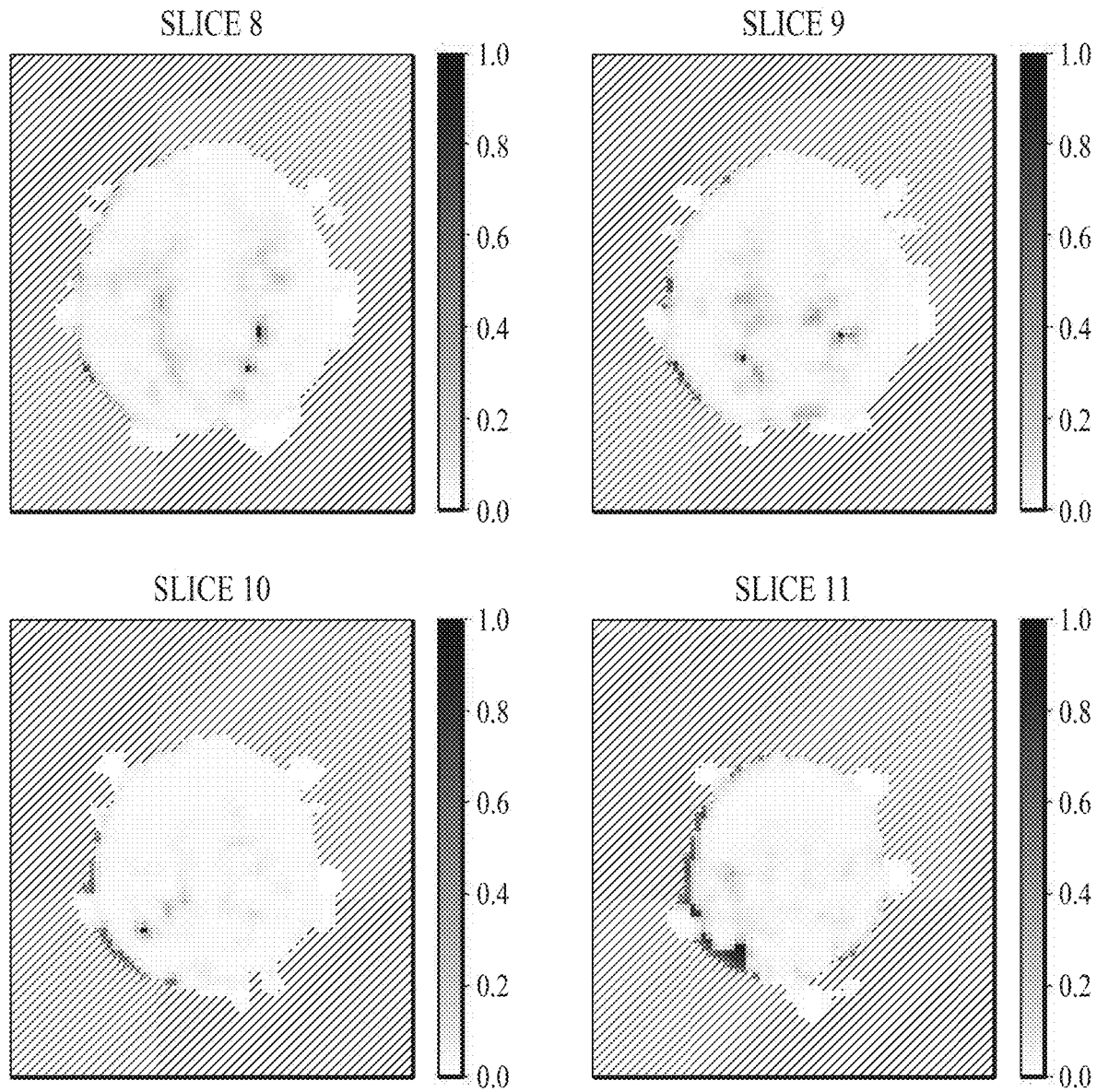

Generation of the voxel-wise NDP ratio colormap further corroborated findings that in patients with anoxic brain injuries, the relationship between ASL and DWI signal was homogeneous throughout the brain (FIGS. 6A-6C). In normal controls, NDP ratio colormap (FIGS. 6D-6F) demonstrated a global heterogeneity evident by the large distribution of DWI/ASL ratios through the brain structures. NDP ratio colormap of the predominately unilateral case, which was an unfortunate non-accidental trauma patient with anoxic brain injury secondary to unilateral carotid occlusion from strangulation, demonstrated uniform color distribution in the affected right hemisphere and heterogeneous color distribution in the non-affected left hemisphere (FIGS. 6G-6I). With future automatic implementation, it is possible that the NDP ratio colormap can be an additional imaging biomarker for anoxic brain injuries, especially in the neonatal population. NDP ratios may have use in other isolated and mixed etiologies, including tumor, stroke, and metabolic diseases.

To simplify the NDP ratio generation for clinical practice, the diagnostic performance of choosing two random ROIs (FIG. 5) is examined. The positivity of the slope of the line between the two points on a graph of ASL versus DWI signal is determined. Positive slopes would be consistent with anoxic injuries. Negative slopes would be consistent with normal patients. The diagnostic performance of this method was less robust than that of the twelve-point ROI linear regression method. This was expected because the inherent heterogeneity of the NDP ratios in the normal population could not be accurately captured by a random two-point selection. If an NDP ratio colormap cannot be obtained while one is trying to confirm the diagnosis of anoxic brain injury, two different basal ganglia or thalamus structures from the opposite hemisphere can be selected for slope determination with reasonable sensitivity (0.78) and specificity (0.71).

Example Methodology

The present inventors retrospectively identified and reviewed medical records for all patients imaged at an institution between 2002 and 2019 whose brain MRI report contained the words "anoxic" or "hypoxic" using an institutional Radiology Search Engine. Anoxic patients were included if their MRI study contained diagnostic ASL perfusion and DWI sequences. Patients were excluded if there was severe motion artifact or the ASL or DWI sequence was otherwise non-diagnostic. Age matched controls imaged with ASL and DWI without a history of anoxic or hypoxic injury were also collected and analyzed. Similar to the anoxic group, control patients were excluded if the ASL or DWI sequence was non-diagnostic. In addition, patients with prior surgeries, intracranial hemorrhage, and ischemic injuries of any age were excluded. Patient age, cause of anoxic injury, and time from anoxic injury to imaging were recorded.

ASL CBF maps are generated using the single phase pulsed ASL clinical sequence available from Philips on 3T Ingenia systems. Example imaging parameters are as follows: 30 dynamics with tag and control pairs; TE, 25 ms; Label delay 900 ms; Flip angle 70 degrees; TR 4000 ms; FOV 24×24 cm; acquisition matrix 68×66 (12 sections; 6 mm thickness; 0.6 mm section gap.). To generate a qualitative grayscale CBF map in some embodiments, a subtraction of the control and labeled pairs is performed. Vascular suppression gradients need not be utilized in some embodiments, e.g., as they are not part of a standard Philips ASL sequence.

Example DWI imaging parameters are as follows TR 5355 ms; TE 81 ms; matrix 116×116; FOV 23×23 cm (3 mm thickness; 0.3 mm section gap). In some embodiments, B0 and B1000 images are used to calculate ADC images using the inline vendor software during image acquisition for automatic ADC map generation. In other embodiments, an open-source post-processing software, such as Horos, may be employed.

Twelve ROIs are manually drawn on the ASL sequence in the caudate, putamen, thalamus, frontal cerebral cortex, and cerebral white matter bilaterally (FIG. 1). An additional ROI was placed in the brain stem and cerebellum and served to normalize the perfusion values; in patients where the brainstem and/or the cerebellum showed restricted diffusion, another area free of involvement was selected for normalization for either white matter, grey matter, or both. Corresponding ROIs are placed on the DWI and ADC images. The signal intensity of each ROI is recorded in gray.

Manually placed ROI regions could have signal interference from surrounding structures, volume averaging, or incompletely matched locations. An automated process for region selection and location matching across sequences could be used in other embodiments.

Example Statistical Analysis

ASL perfusion, DWI, and ADC measurements for each ROI are normalized using the ROI signal intensity in the cerebellum or the brain stem, for grey matter and white matter, respectively. A linear best fit was performed between the normalized DWI and the normalized ASL values and the slope recorded, allowing up to 25% outlier identification. Graphs of the best-fitted line slopes and their respective $R^2$ values are generated with a pre-determined $R^2$ cutoff of 0.70. A similar analysis is performed using the normalized ADC measurements.

The relationship between the estimated time interval from inciting event to imaging and the linear regression slopes as well as $R^2$s is examined to determine the dependence on the timing of imaging. Calculations are also made to determine the dependence on the number of ROI measurements. Two random raw (non-normalized) DWI and ASL ROIs are selected for each patient and the slope was calculated using the two points. Combinations of two ROI selections are segregated into three different groups: both ROIs within basal ganglia and thalamus, either ROI within basal ganglia and thalamus, or no ROI within basal ganglia and thalamus.

Data is presented as mean±standard error of the mean (SEM) and frequency (percentage) for numerical and categorical variables, respectively. Analysis is completed using Fisher's exact test and Mann-Whitney nonparametric t-test. A two-tailed p-value less than 0.05 was considered significant.

Example Diffusion to Perfusion (DP) Ratio Brain Image Generation

In this disclosure, a brain image may include data, an array of intensities, color printout, image file, array of ratios, or any other data structure capable of representing features of brain. More specifically, a brain image map is an image illustrating brain regions and associated features (intensities, ratios, colors, and other features).

In some embodiments, generating a DP ration brain image entails receiving MRI data, in which the receiving is achieved through a network interface or direct data transfer. The MRI data includes perfusion and diffusion sequences. Depending on the context, the term sequence means a particular setting of pulse sequences and pulsed field gradients, resulting in a particular image appearance, though it also refers to the particular image or set of images generated using that particular MRI sequence protocol setting. Thus, in some embodiments, digital imaging and communications in medicine (DICOM) files of the perfusion (ASL or equivalent sequences) and diffusion (DWI or equivalent sequences) are retrieved.

In some embodiments, the received sequences are co-registered using DICOM dictionary parameters. Other standardized co-registration toolbox, including but not exclusive to ANTs, Elstastix, NiftiReg, and FSL, or customized imaging processing pipeline, can be used for co-registration. For example, co-registration is sometimes performed because the perfusion and diffusion sequences may have been generated independently, in which case the same brain locations are represented at different image locations. Thus, co-registration attempts to match the locations from different coordinates.

In some embodiments, resampling can be performed, if necessary, to obtain image sequences with equal slice thickness. For example, resampling is sometimes performed so at to attempt to match scale, i.e., matching image Voxel size. More generally, digital images may represent a rectangular grid of evenly spaced pixels, in which case resampling is the mathematical technique, such as interpolation, used to create a new version of the image with a different width and/or height in pixels. Increasing the size of an image is called upsampling; reducing its size is called downsampling.

In some embodiments, to decrease the impact of punctate heterogeneous noisy signals, an optional smoothing function is applied. For example, a Gaussian smoothing function with a of one pixel and window of five pixels or an edge preserving smoothing function such as an anisotropic diffusion filter can applied to both sequences. Other example functions include Laplacian, Kernel, and spline smoothing.

Once the image data is processed, ratios may be calculated. The NDP ratio colormap is generated using the ratio of the Z-score normalized DWI and ASL sequences (DWI can serve as either the denominator or the numerator, c.f., FIGS. 6A-6I and 7A-7I).

To prepare the calculated data for display (e.g, presentation or printing), a standard "JET" spectrum colormap is implemented to represent the spectrum of the NDP ratios on the colormap. Other standardized colormaps, including but not exclusive to "BRG," "COOLWARM," and "HOT," or customized colormaps may be substituted for representation.

Example Experimental Results 45 patients with anoxic injuries were initially identified using our institutional Radiology Search Engine from 2002 to 2019 with two-reader confirmation. Nine patients were excluded due to non-diagnostic imaging sequences; one patient was excluded due to remote injury (imaging was obtained 253 days after initial inciting event). The remaining 35 patients with anoxic injuries had imaging ranging from 0 to 14 days after the reported inciting event with mean of 3.8±0.5 days. 36 age-matched patients with a normal MRI had imaging performed between September 2010 and May 2019. Patient characteristics of the anoxic group and the normal group are shown in Table 1.

TABLE 1

Patient characteristics of the anoxic injury group and the normal control group

| Variable | Anoxic (n = 35) | Normal (n = 36) | p value |
|---|---|---|---|
| Age (years) | 21.1 ± 4.4 | 26.5 ± 2.7 | 0.03 |
| Gender (Female) | 16 (45.7%) | 15 (41.7%) | 0.73 |
| Survived | 13 (37.1%) | | |
| Interval to imaging (days) | 3.8 ± 0.5 | | |
| Received CPR | 15 (42.9%) | | |
| CPR time (minutes) | 22.7 ± 4.3 | | |
| Witnessed Seizure | 8 (22.9%) | | |
| Neonatal hypoxic-ischemic encephalopathy (NHIE) | 10 (28.6%) | | |
| Mechanical (asphyxiation, hanging, drowning, etc.) | 8 (22.9%) | | |

Figure 2A:
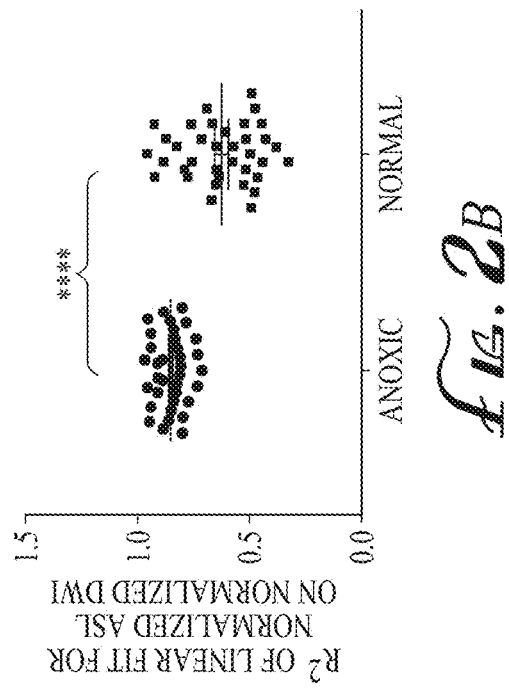
Figure 2C:
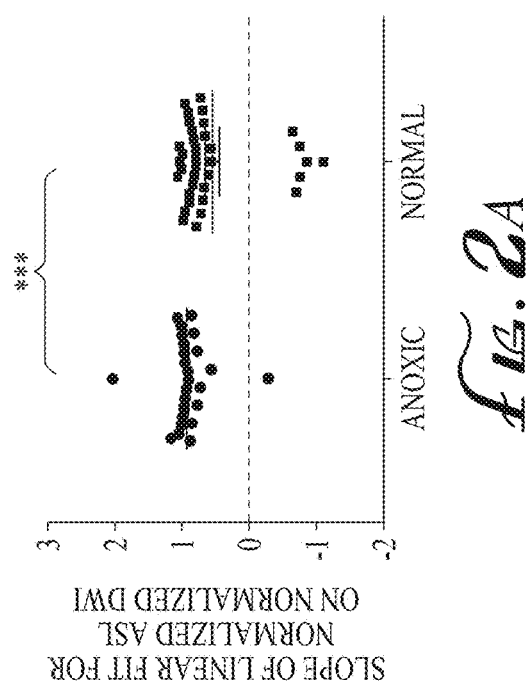
Figure 2B:
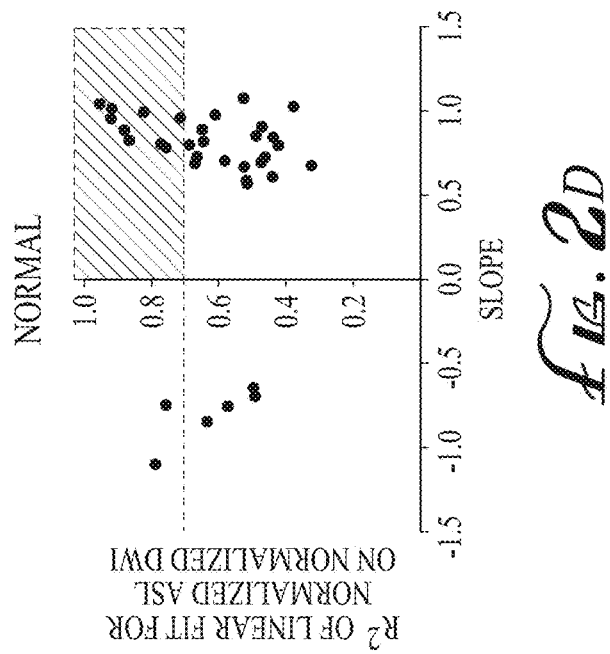
Figure 2D:
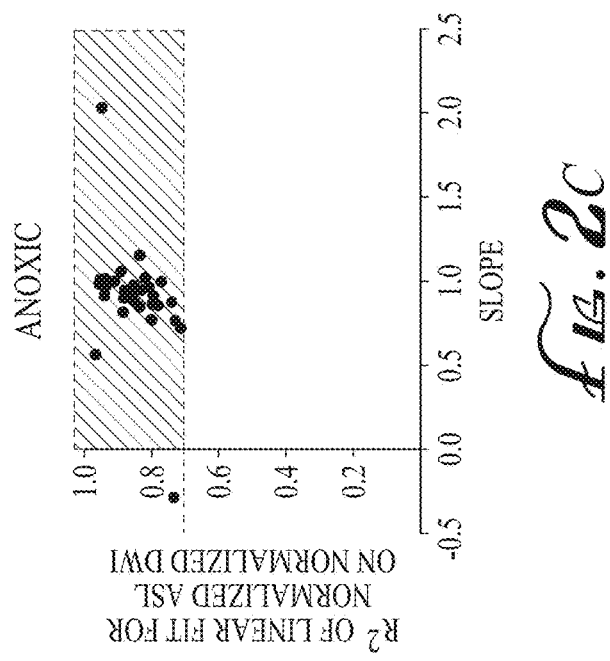

A linear regression between the normalized DWI and normalized ASL density values was applied with the slope and $R^2$ values recorded. Best fitted lines of anoxic injuries demonstrated significantly higher slopes of 0.93±0.05, compared to that of normal controls at 0.59±0.11, p=0.0001 (FIG. 2A). Best fitted lines of anoxic injuries also had significantly higher $R^2$s of 0.85±0.01, compared to 0.62±0.03 of normal controls, with p<0.0001 (FIG. 2B). Scatter plots of the best fitted lines $R^2$ and their corresponding slopes were generated (FIGS. 2C and 2D).

Using a combinatory cutoff of slope higher than 0 and $R^2$ higher than 0.70, the following diagnostic characteristics for anoxic injuries were obtained: sensitivity of 0.97 (95% confidence interval (CI): 0.85-1.00), specificity of 0.75 (95% CI: 0.59-0.86), positive predictive value of 0.79 (95% CI: 0.65-0.89), and negative predictive value of 0.96 (95% CI: 0.83-1.00). Contingency table is shown in Table 2, with Fisher's exact test p<0.0001.

TABLE 2

Contingency table of normalized DWI and normalized ASL linear regression for the diagnosis of anoxic injury using a combinatory cutoff of slope higher than 0 and $R^2$ higher than 0.70. Fisher's exact test p value < 0.0001.

| | CASE COUNT TOTAL % COL % ROW % | | |
|---|---|---|---|
| | ANOXIC | NORMAL | TOTAL |
| POSITIVE SLOPE AND $R^2 > 0.70$ | 34<br>47.89%<br>97.14%<br>79.07% | 9<br>12.68%<br>25.00%<br>20.93% | 43<br>—<br>60.56%<br>— |
| NEGATIVE SLOPE OR $R^2 < 0.70$ | 1<br>1.41%<br>2.86%<br>3.57% | 27<br>38.03%<br>75.00%<br>96.43% | 28<br>—<br>39.44%<br>— |
| TOTAL | 35<br>—<br>—<br>49.30% | 36<br>—<br>—<br>50.70% | 71<br>100%<br>—<br>— |

A similar analysis was performed using the ADC ROI measurements with the following diagnostic characteristics for anoxic injuries: sensitivity of 0.49 (95% confidence interval (CI): 0.33-0.64), specificity of 0.86 (95% CI: 0.71-0.94), positive predictive value of 0.77 (95% CI: 0.57-0.90), and negative predictive value of 0.63 (95% CI: 0.49-0.75) (see generally FIGS. 3A-3D). Contingency table was shown in Table 3, with Fisher's exact test p=0.002.

TABLE 3

Contingency table of normalized ADC and normalized ASL linear regression for the diagnosis of anoxic injury using a combinatory cutoff of slope less than 0 and $R^2$ higher than 0.70. Fisher's exact test p value = 0.002.

| | CASE COUNT TOTAL % COL % ROW % | | |
|---|---|---|---|
| | ANOXIC | NORMAL | TOTAL |
| NEGATIVE SLOPE AND $R^2 > 0.70$ | 17<br>23.94%<br>48.57%<br>77.27% | 5<br>7.04%<br>13.89%<br>22.73% | 22<br>—<br>30.99%<br>— |
| POSITIVE SLOPE OR $R^2 < 0.70$ | 18<br>25.35%<br>51.43%<br>36.73% | 31<br>43.66%<br>86.11%<br>63.27% | 49<br>—<br>69.01%<br>— |
| TOTAL | 35<br>—<br>—<br>49.30% | 36<br>—<br>—<br>50.70% | 71<br>100%<br>—<br>— |

Figure 4B:
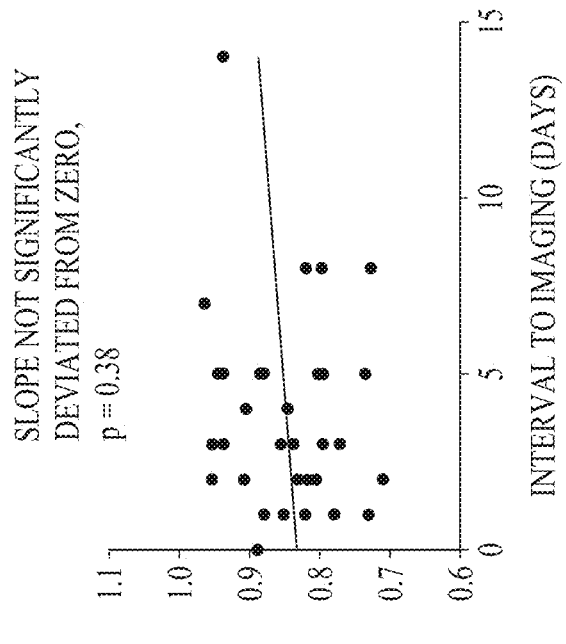
FIGS. 4A and 4B are linear regression plots showing no significant linear dependence between slopes and interval to imaging (FIG. 4A), nor between $R^2$ and interval to imaging (FIG. 4B), using DWI and ASL sequence.
Figure 4A:
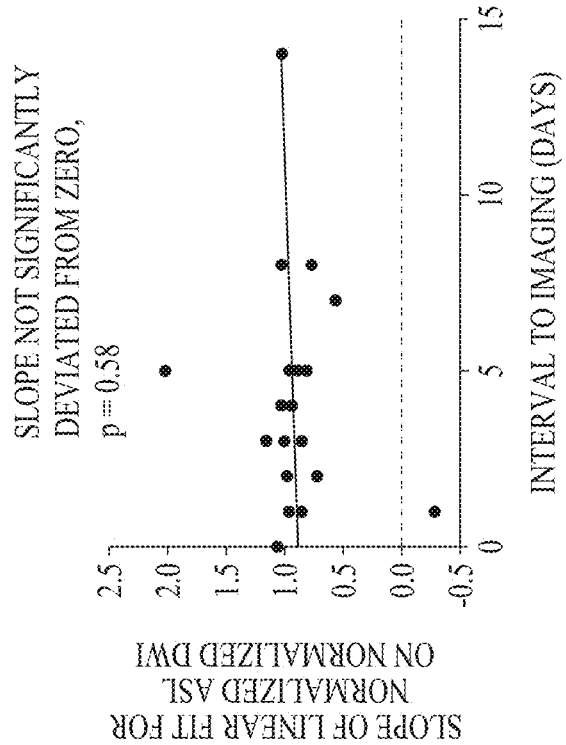

In order to determine the effects of time, the relationship between the time interval from inciting event to imaging and the linear regression slopes and $R^2$ was examined (see FIGS. 4A and 4B). Both failed to demonstrate significantly non-zero slopes (y=0.01055*x+0.8847 with p=0.58 and y=0.003945*x+0.8327 with p=0.38, for linear regression slopes and $R^2$, respectively). Thus, both exhibited positive trends.

Figure 5:
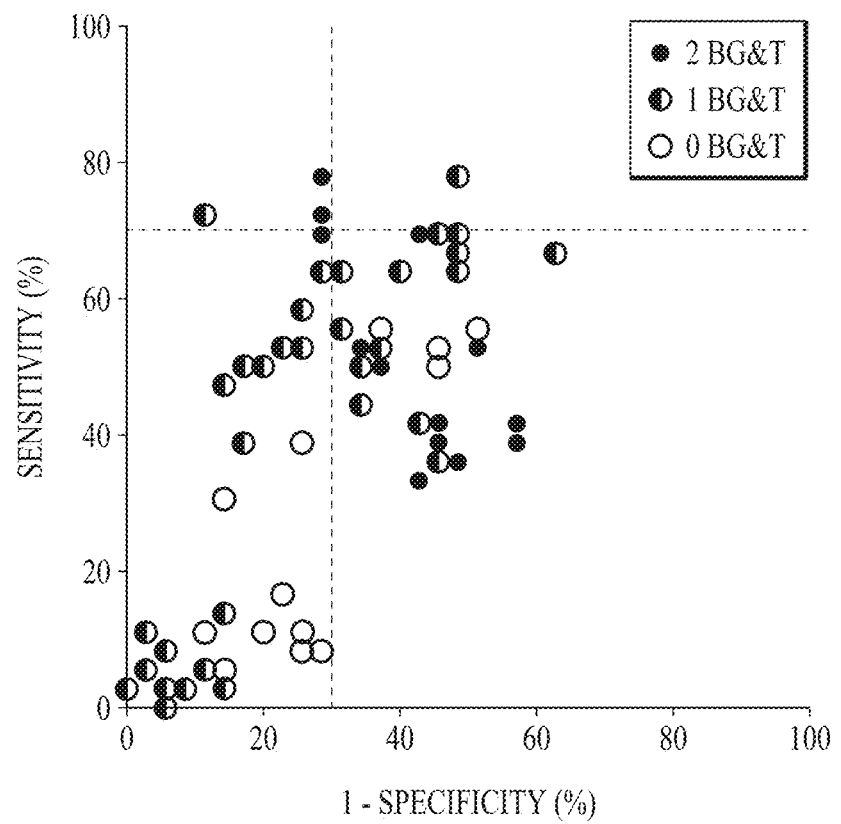
FIG. 5 is a scatterplot for two-point ROI analyses providing reasonable sensitivity and specificity although the diagnostic performances are highly variable, as shown with 1 basal ganglia/thalamus and non-basal-ganglia/thalamus selection and 3 double basal ganglia/thalamus selections reaching 70% cutoffs in both sensitivity and specificity.

Permutations of possible "12 select 2" ($C_2^{12}$=66) ROI raw (non-normalized) DWI and ASL signal densities were examined to determine the dependence on ROI selection. Using a cutoff of positive versus negative slopes for anoxic and normal diagnostic predictions, specificity and sensitivity were calculated. Data was segregated into three groups: both ROIs within basal ganglia and thalamus, either ROI within basal ganglia and thalamus, or no ROI within basal ganglia and thalamus (FIG. 5). A combination of caudate and contralateral putamen was able to achieve a sensitivity of 0.78 and specificity of 0.71. Another combination, putamen and contralateral cortex, showed a sensitivity of 0.72 and specificity of 0.89. The overall diagnostic performance of this "two-location ROI" method was less robust compared to that of the "twelve-location ROI linear regression" method (p<0.0001 for sensitivity and p=0.03 for specificity).

Figure 6D:
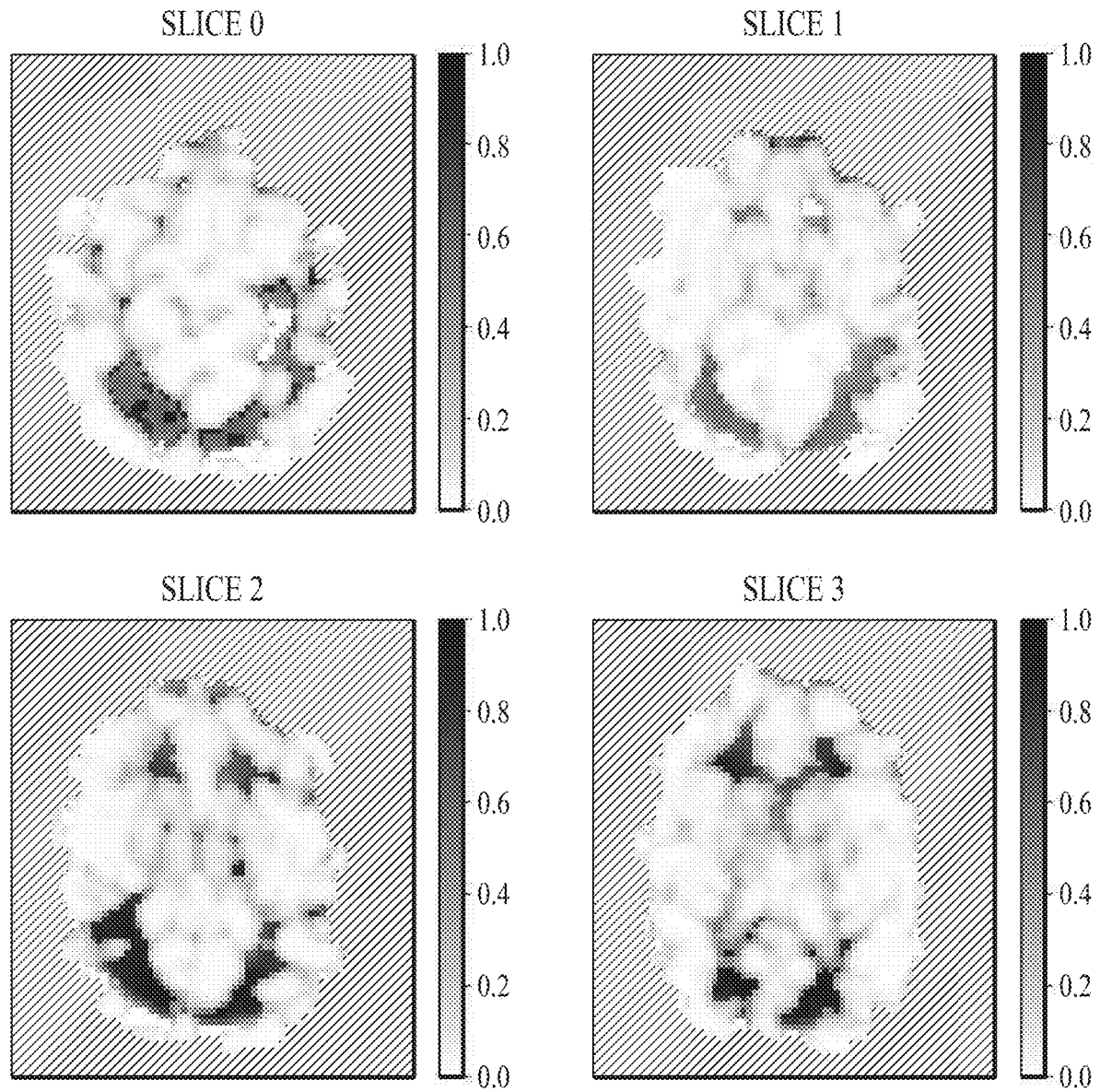
Figure 6E:
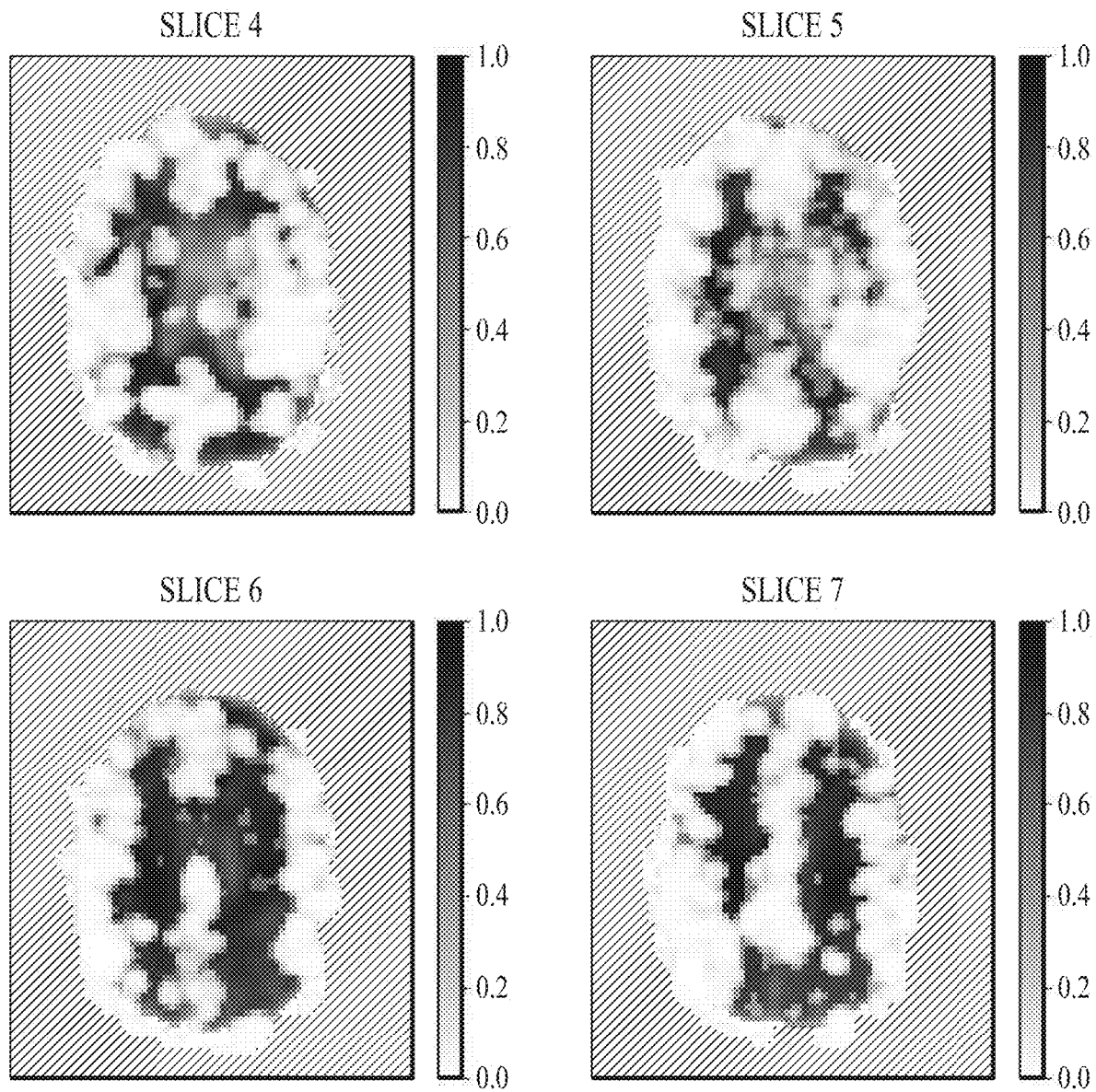
Figure 6F:
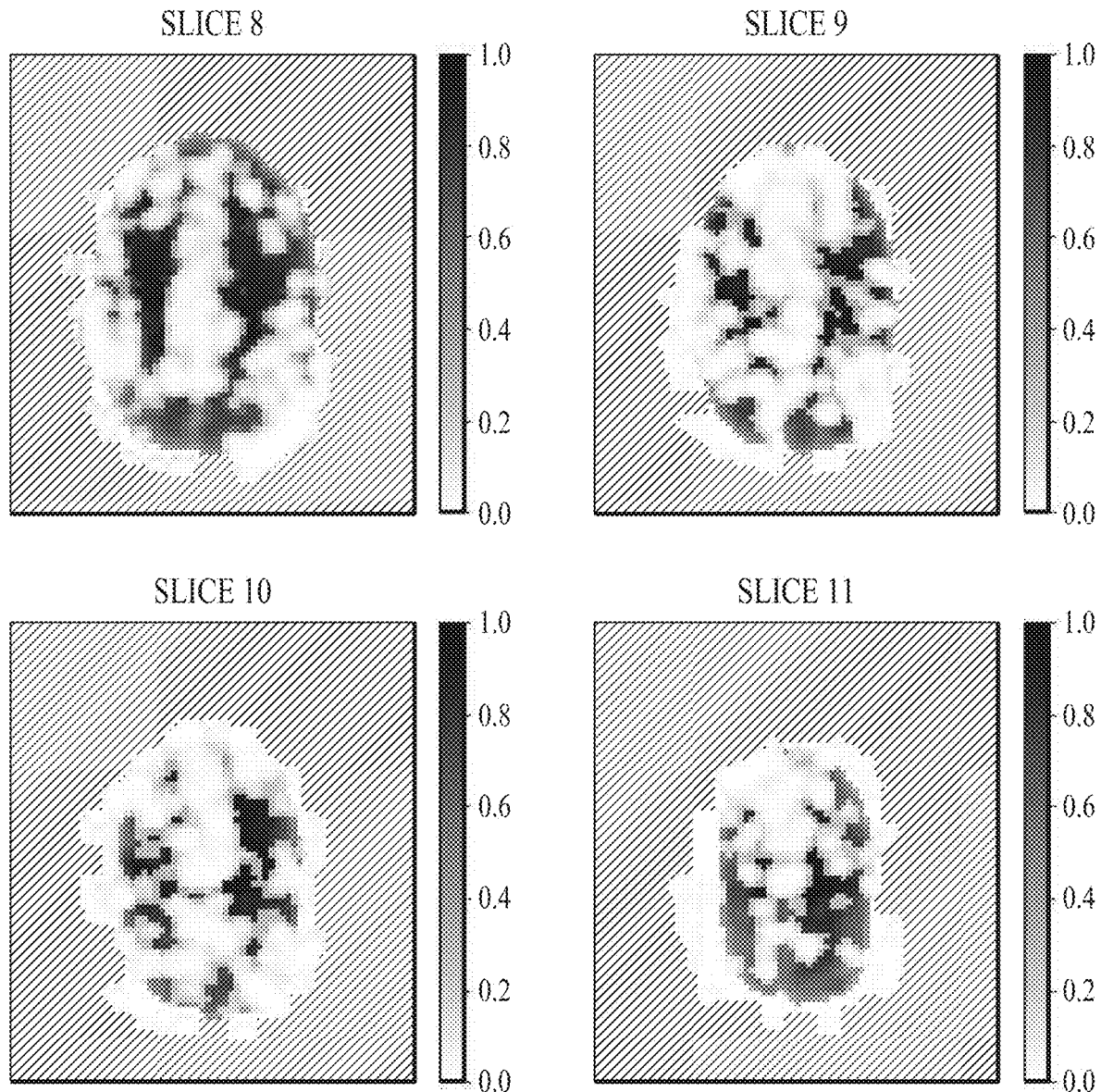
Figure 6G:
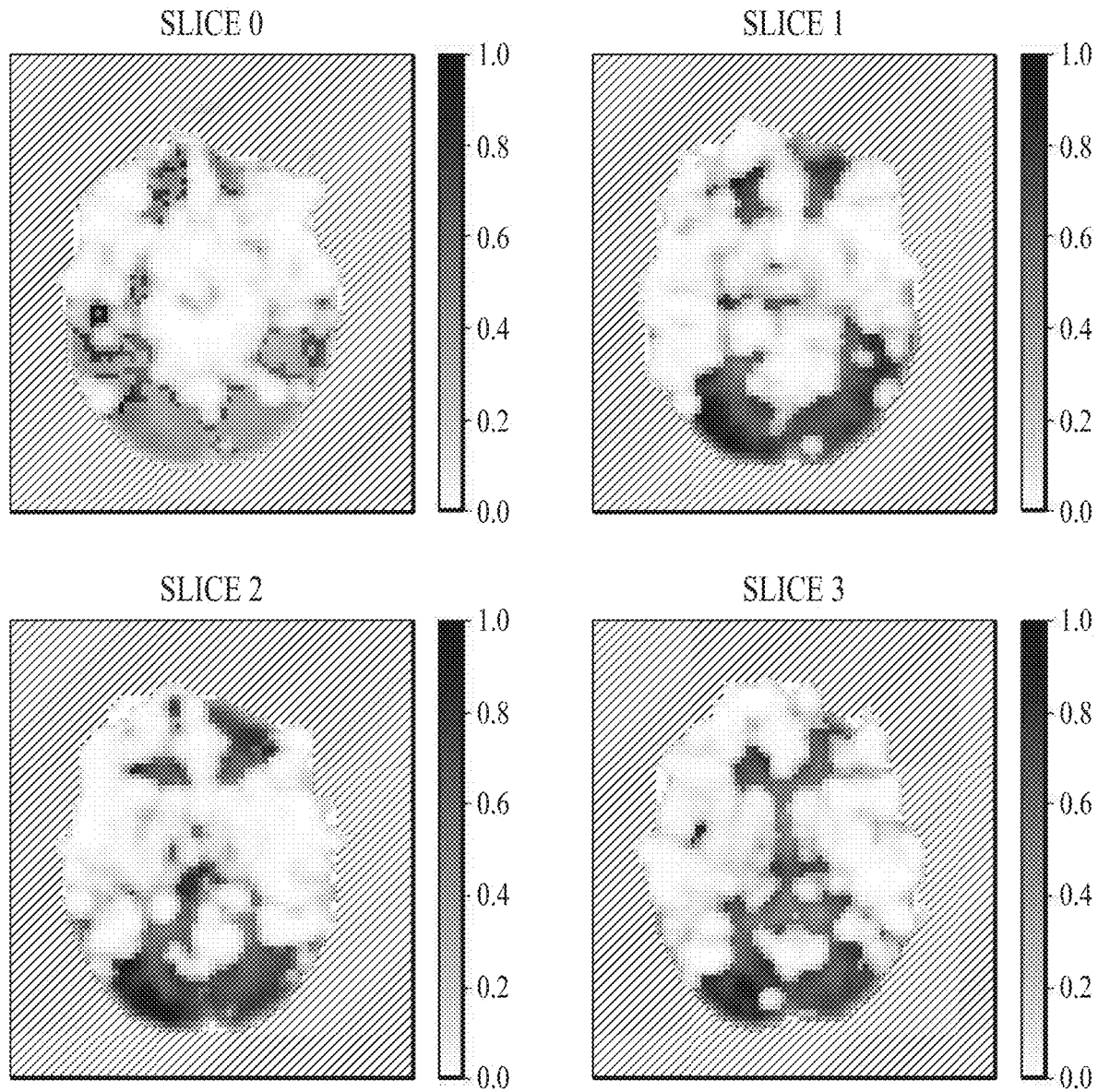
Figure 6H:
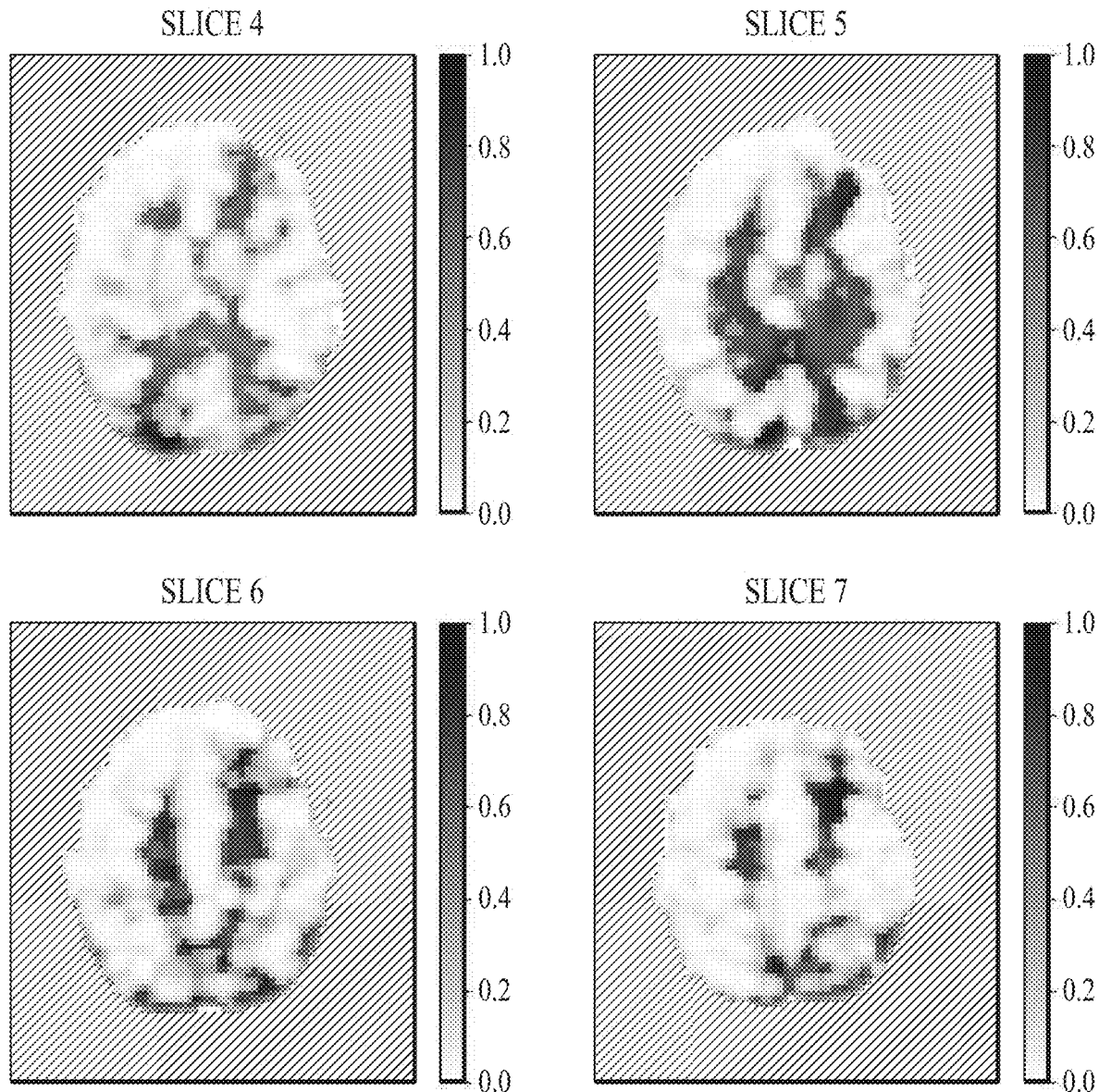
Figure 61:
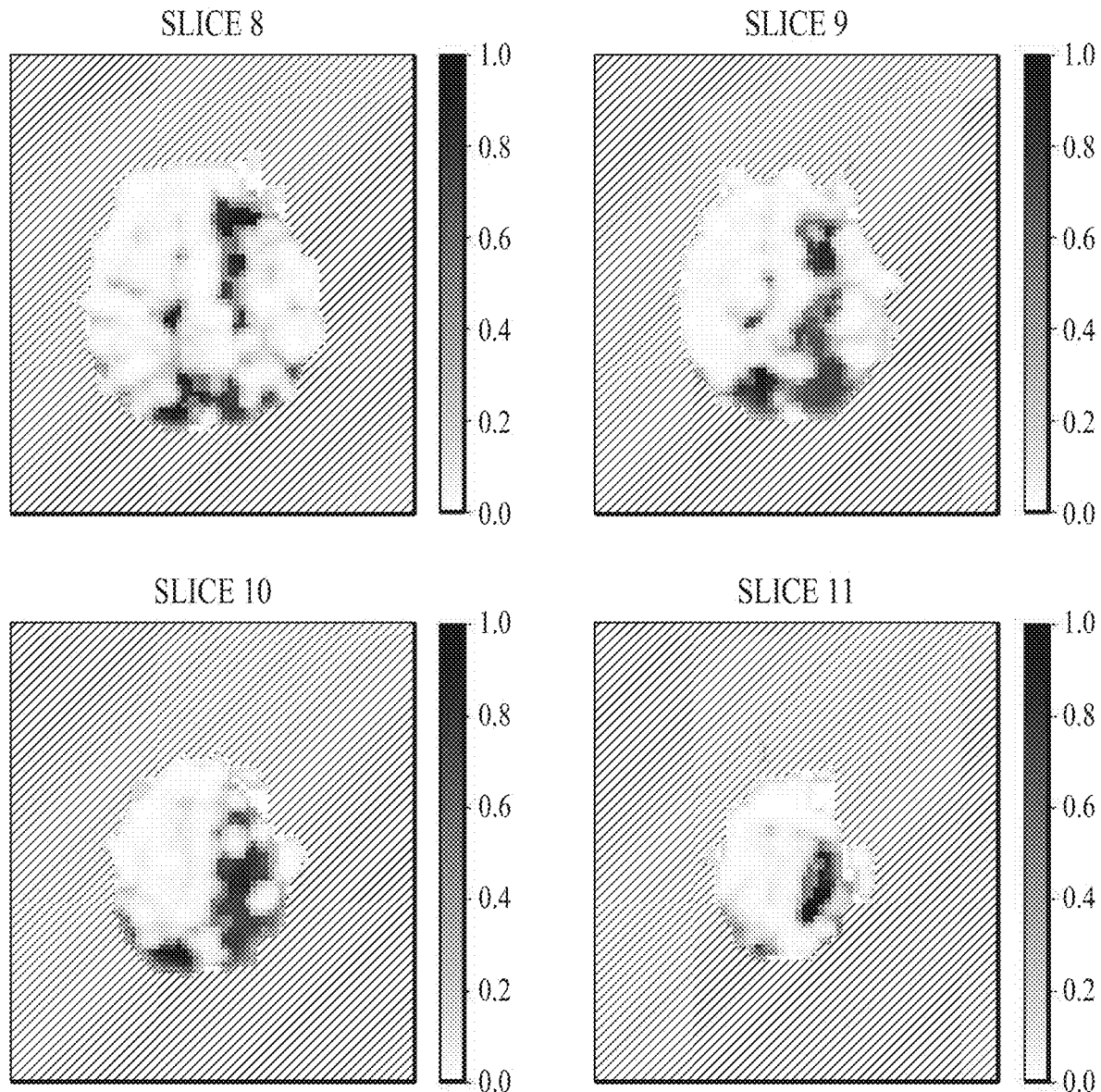
Figure 7A:
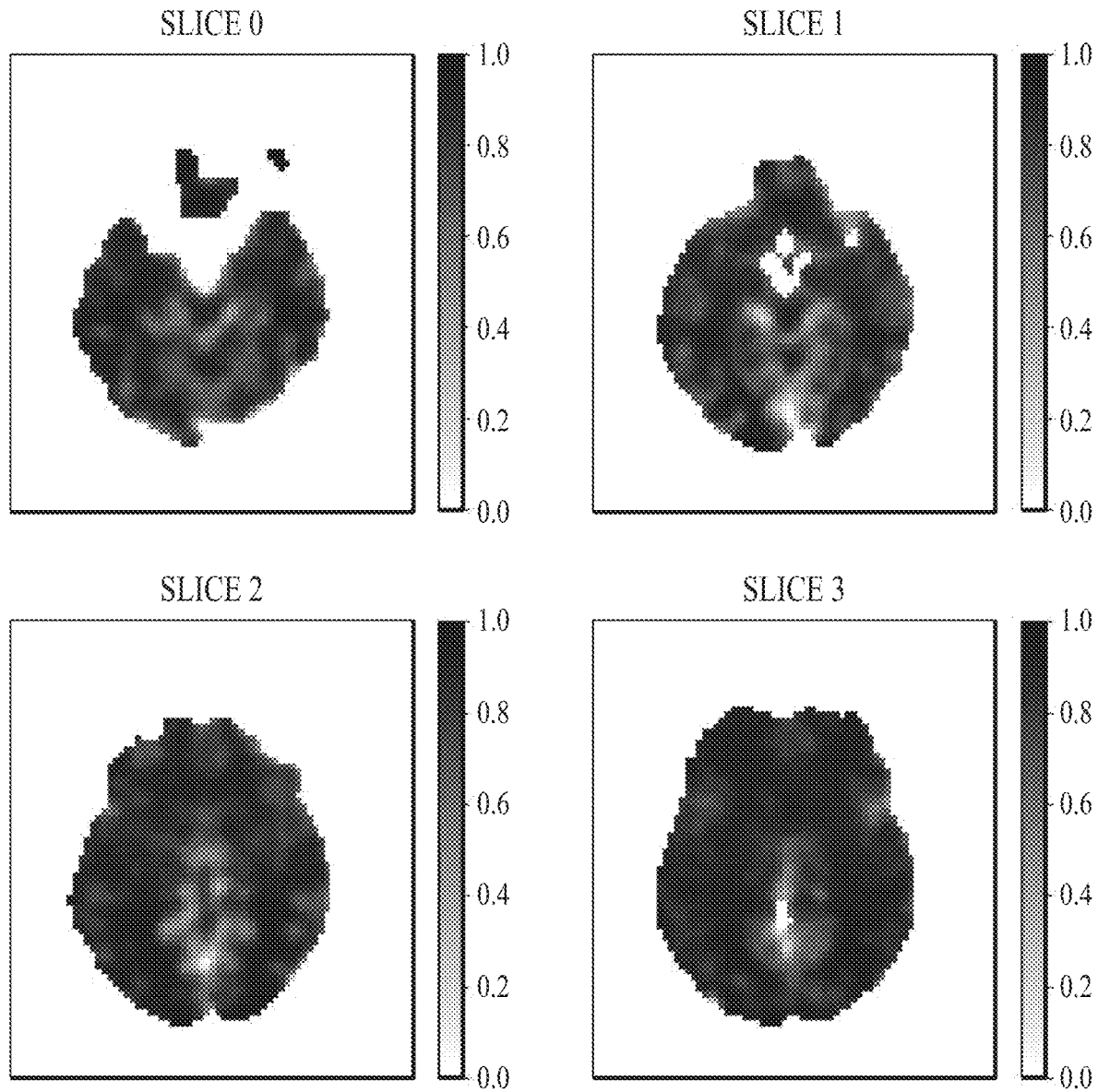
Figure 7B:
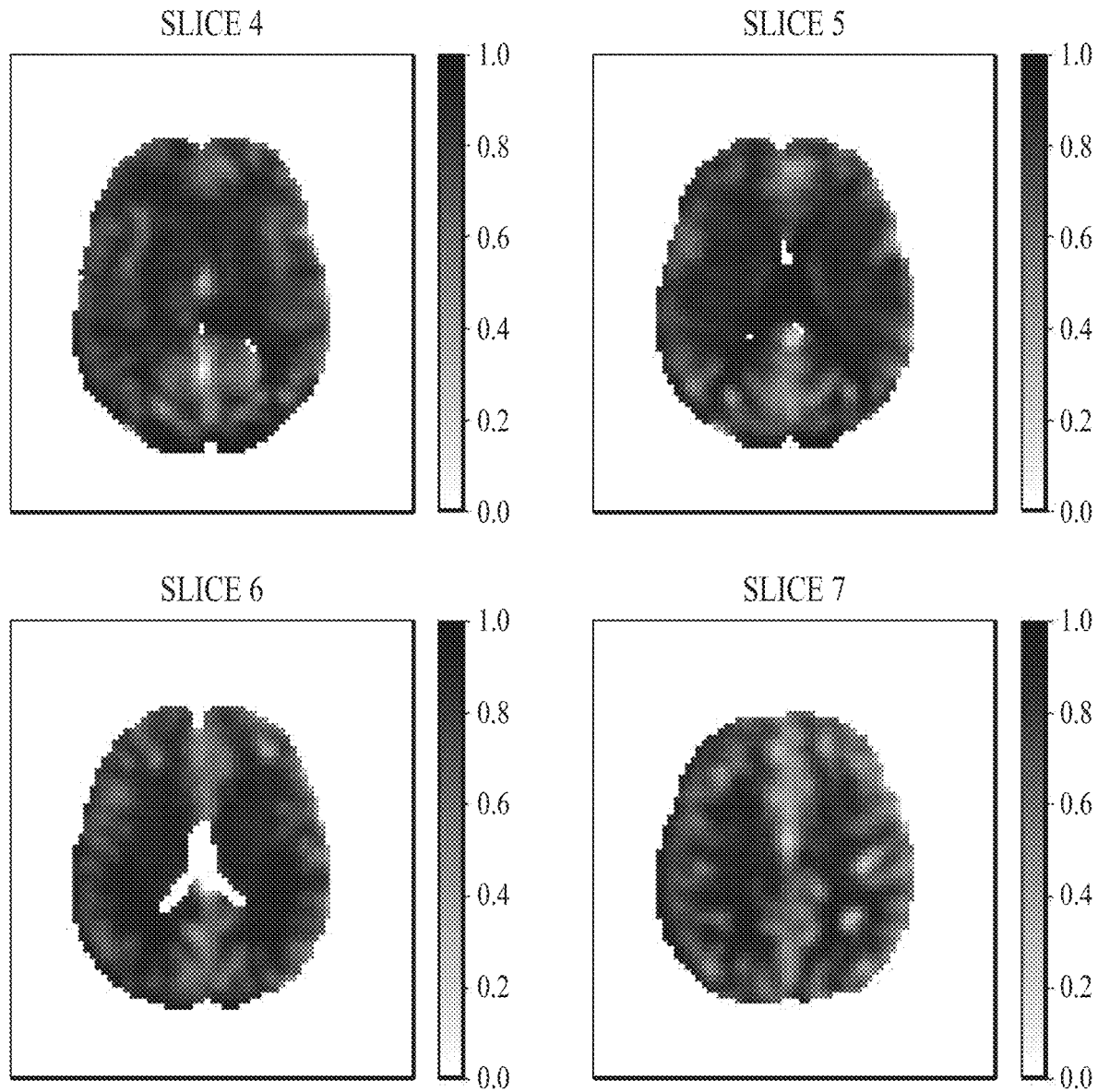
Figure 7C:
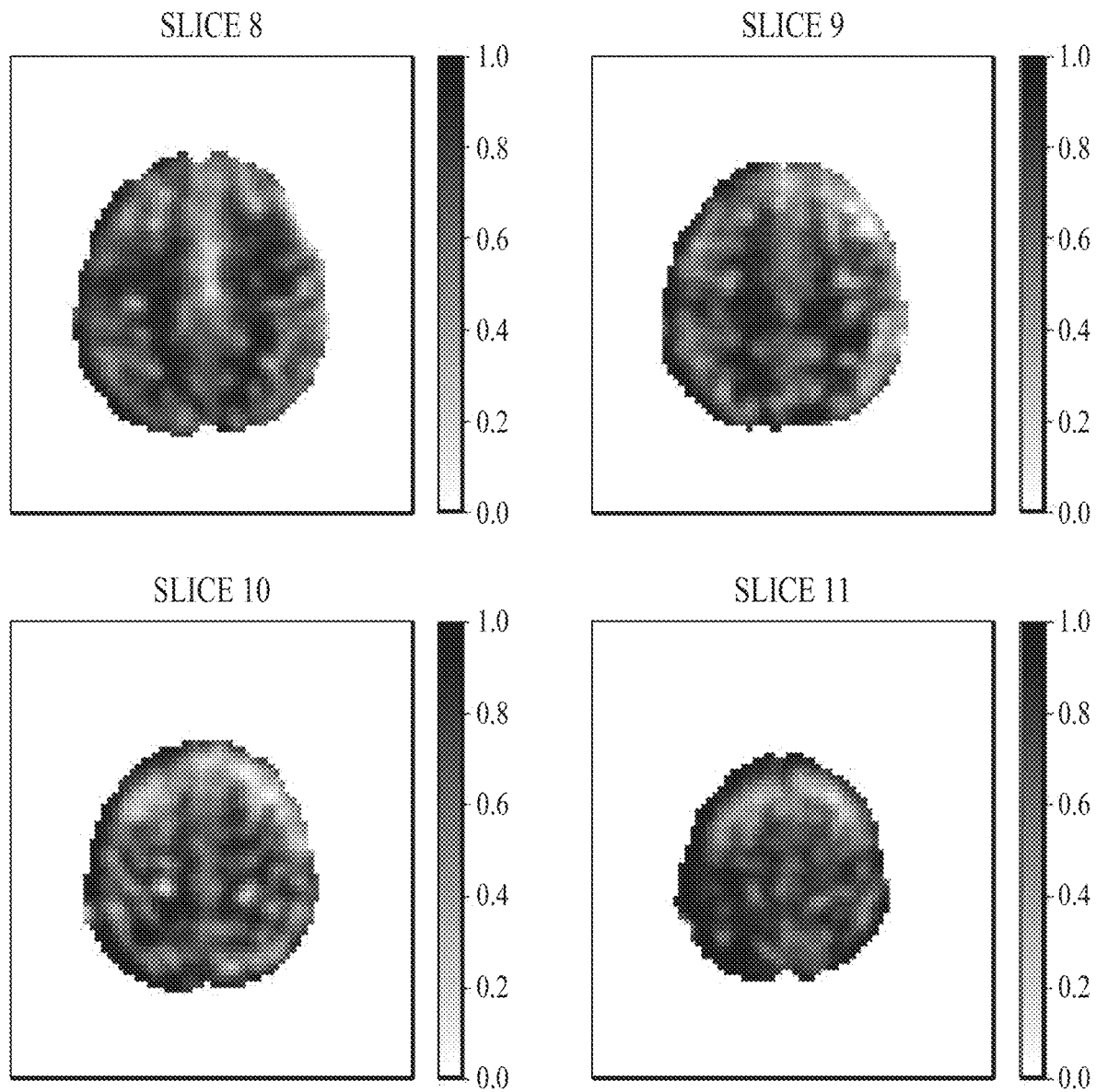
Figure 7D:
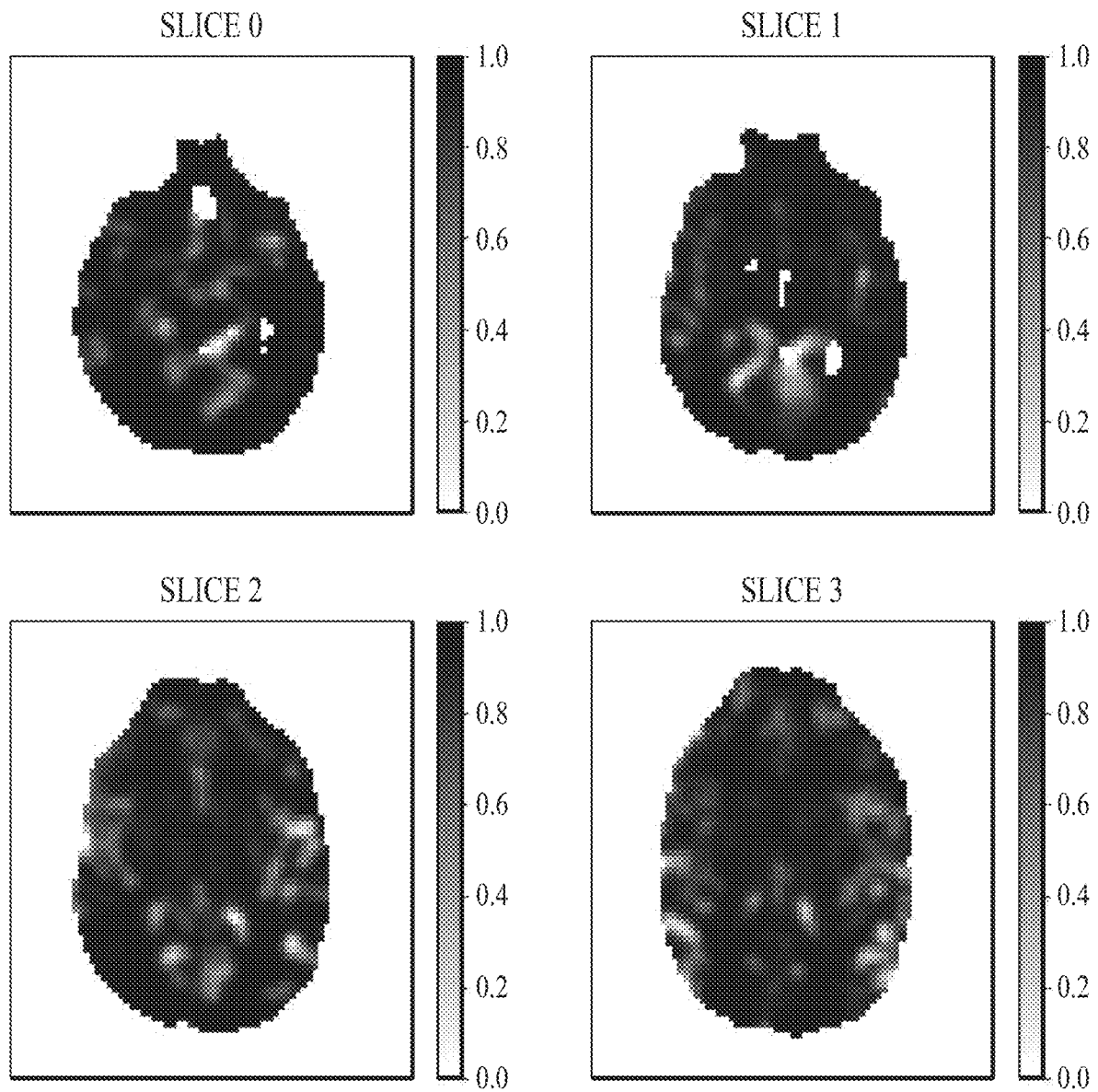
Figure 7E:
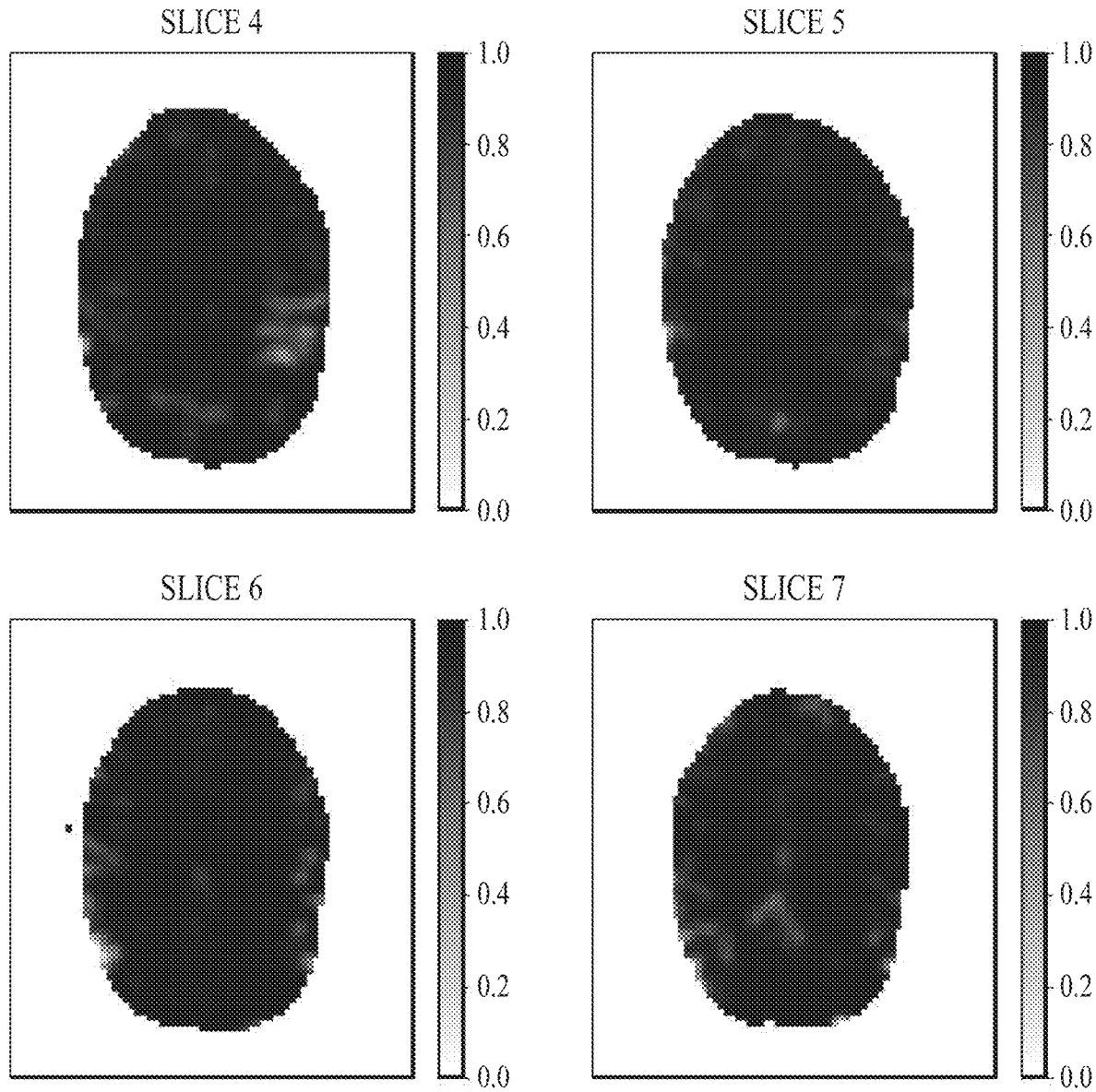
Figure 7G:
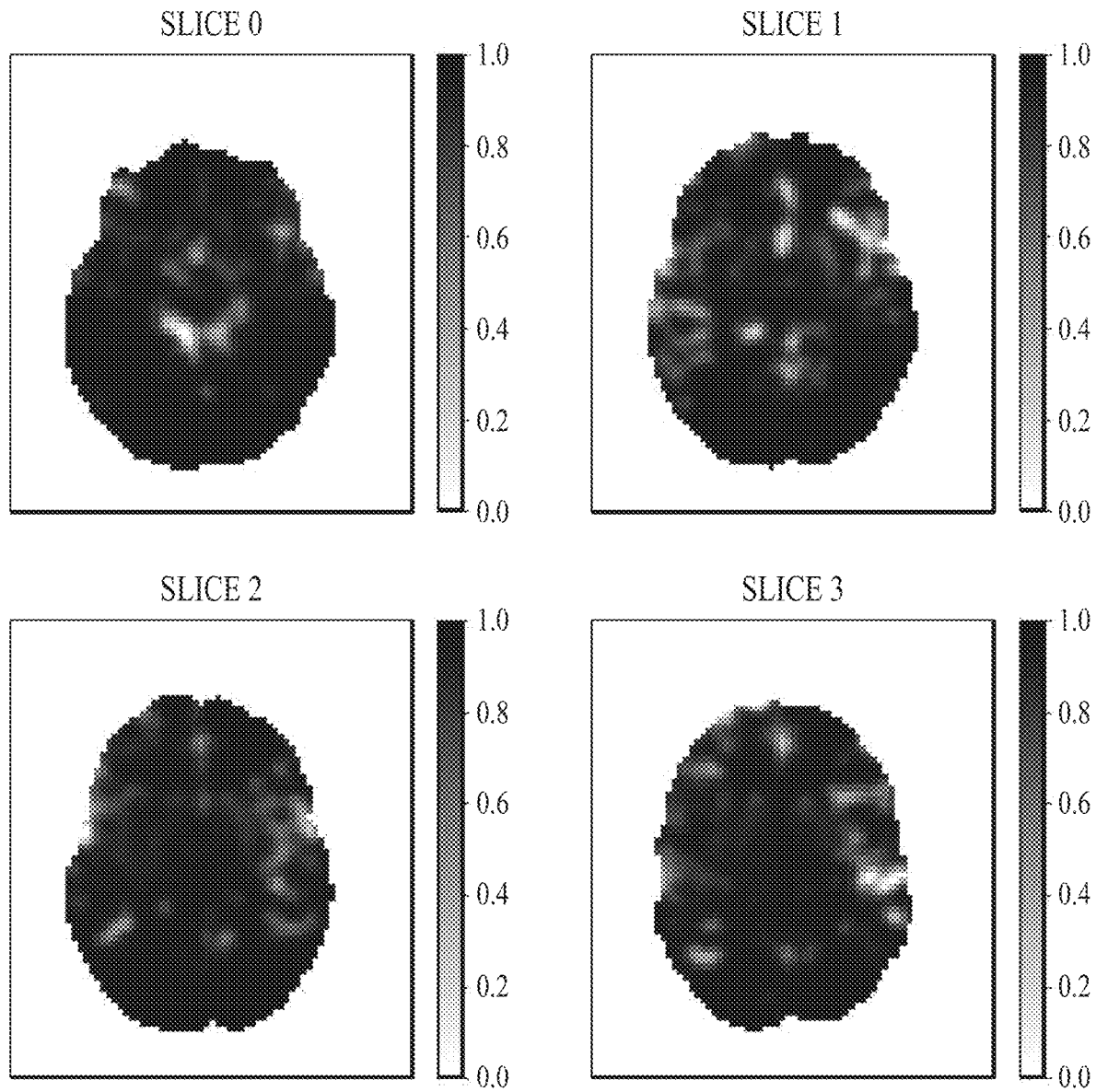
Figure 7H:
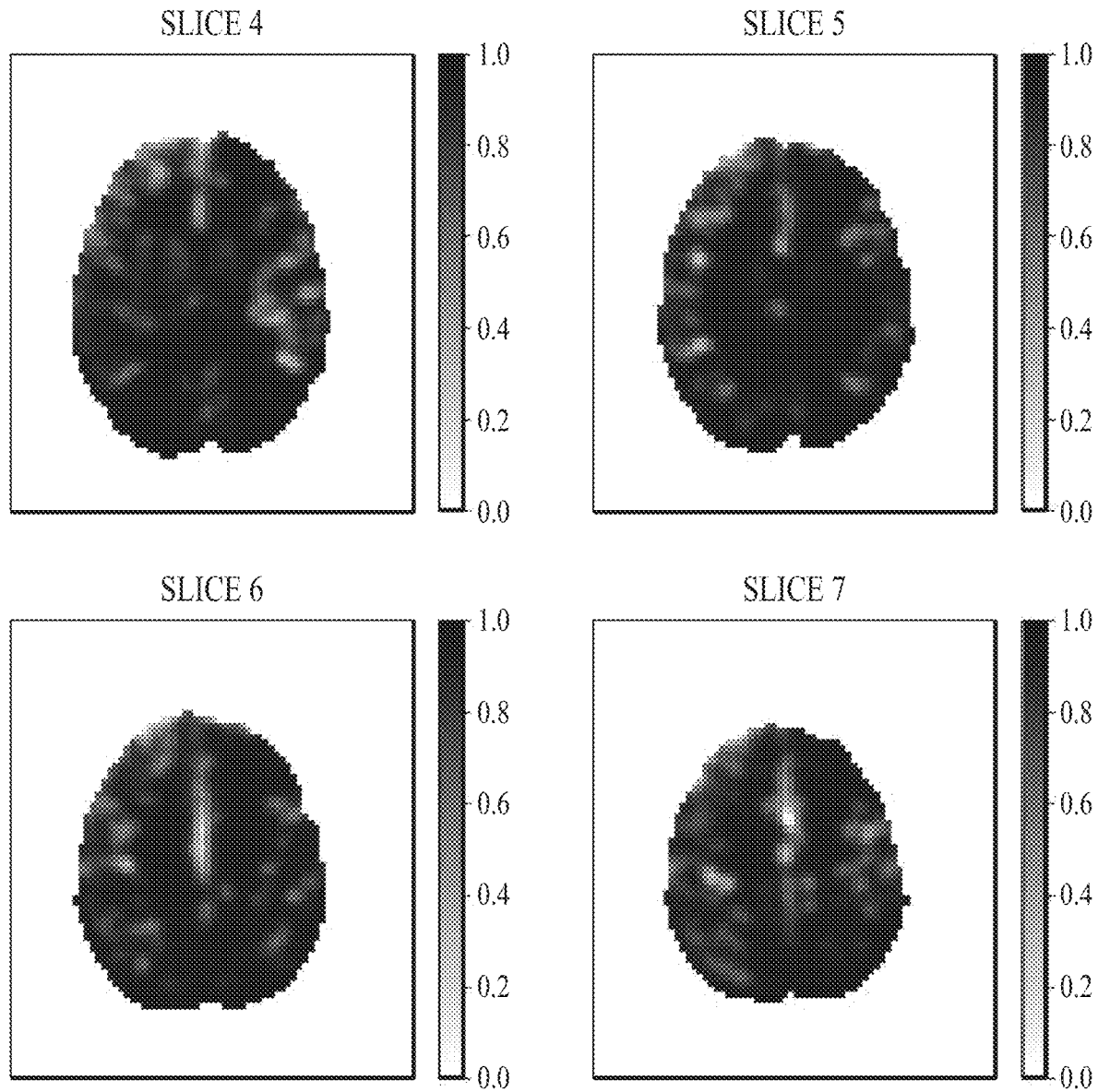
Figure 71:
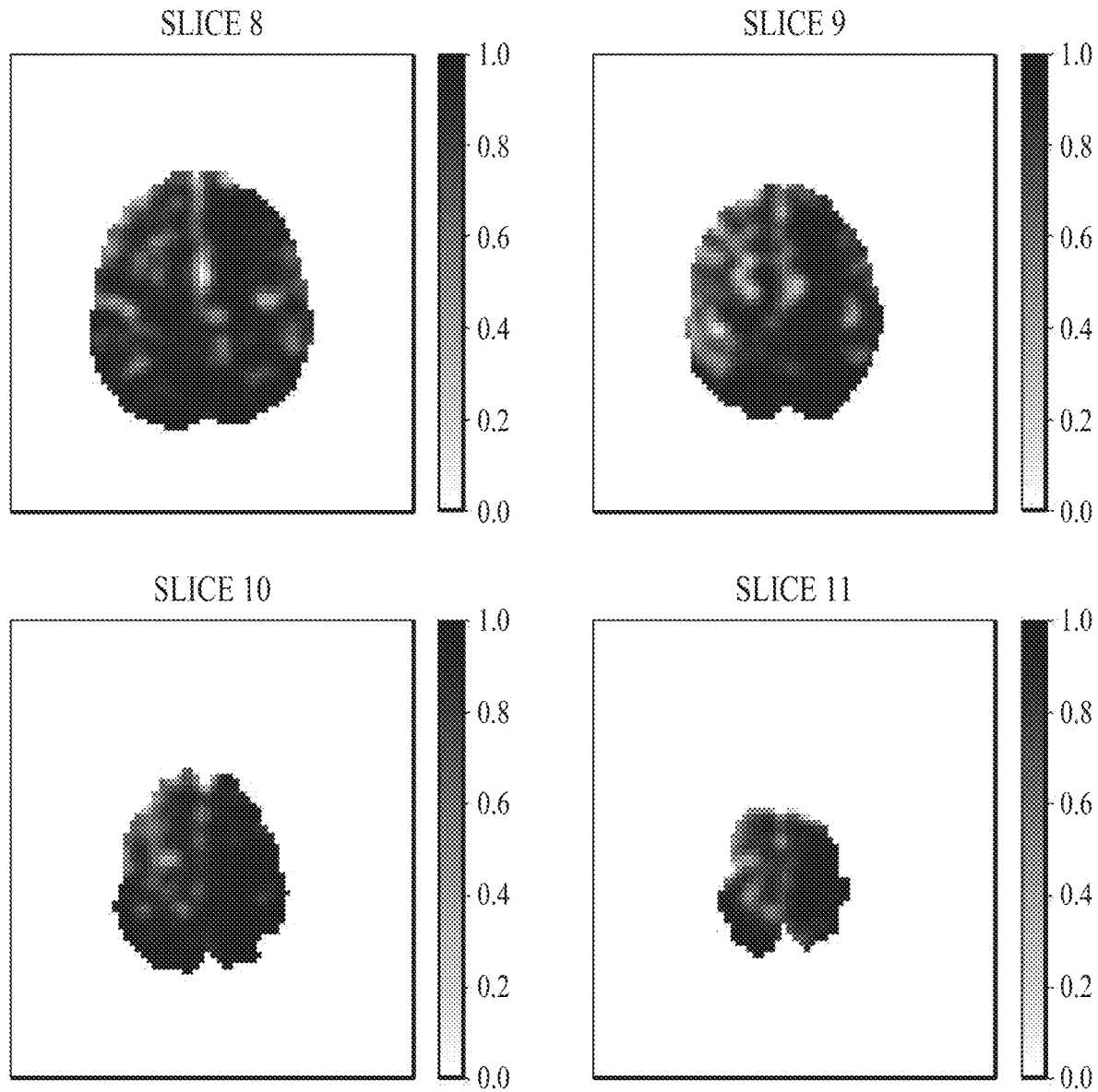

The NDP ratio colormap was generated using the resampled, Gaussian smoothed, and Z-score normalized DWI sequence and the Gaussian smoothed, and Z-score normalized ASL sequence (see generally, FIGS. 6A-6I). NDP ratio colormap of anoxic injuries demonstrate homogeneous color distribution throughout the brain (FIGS. 6A-6C). NDP ratio colormap of normal controls demonstrated heterogeneous color distribution bilaterally (FIGS. 6D-6F). Highlighting the differences between the anoxic and non-anoxic pattern, the NDP ratio colormap of predominately unilateral anoxic injury secondary to strangulation demonstrated homogenous signals in the primarily affected right hemisphere and heterogeneous signals in the preserved left hemisphere (FIGS. 6G-6I).

FIGS. 7A-7I show that the aforementioned maps can also be generated by reversing the ratios such that perfusion values are in the numerators and diffusion values are in the denominators. Under either approach, division by zero may be addressed by assigning minute levels in place of zero signal values. Moreover, skilled persons will appreciate that the term NDP generically refers to either approach, i.e., normalized ratios between diffusion and perfusion, and the letter "D" preceding the letter "P" is of no moment.

Example Device Configured for Generating Anoxic/Hypoxic Brain Imaging Maps

Figure 8:
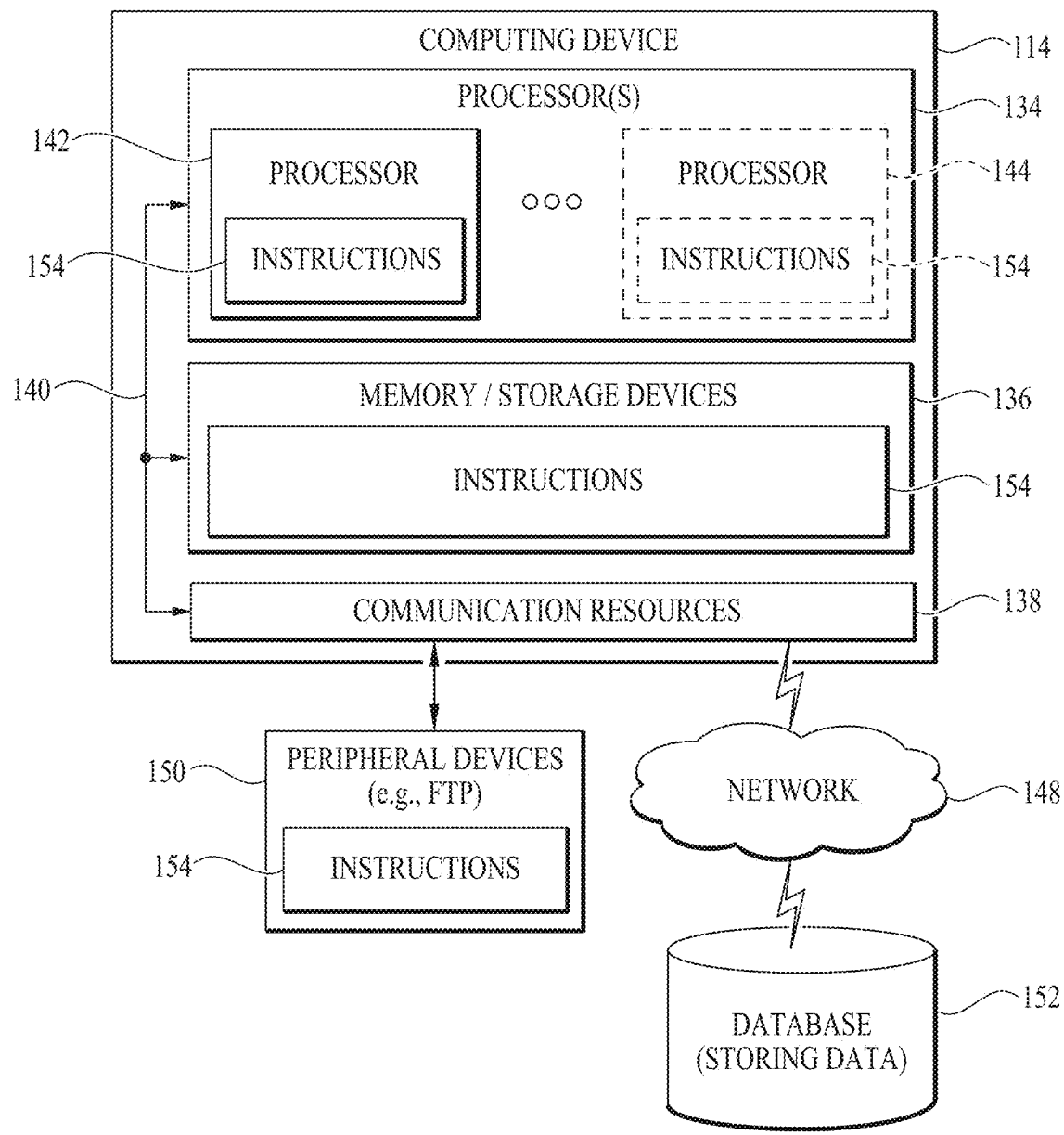
FIG. 8 is a block diagram of a computing device, according to one embodiment.

Embodiments described herein may be implemented in any suitably configured computing hardware and software resources of computing device 114, as shown in FIG. 8. And various aspects of certain embodiments may be implemented using hardware, software, firmware, or a combination thereof, for reading instructions from a machine- or computer-readable non-transitory storage medium and thereby performing one or more of the methods realizing the disclosed algorithms and techniques. Specifically, computing device 114 includes one or more microcontrollers 134, one or more memory/storage devices 136, and one or more communication resources 138, all of which are communicatively coupled via a bus or other circuitry 140.

Microcontroller(s) 134, may include, for example, a processor 142 (shared, dedicated, or group), an optional processor (or additional processor core) 144, an ASIC or other controller to execute one or more software or firmware programs, a combinational logic circuit, or other suitable components that provide the described functionality.

Memory/storage devices 136 may include main memory, cache, flash storage, or any suitable combination thereof. Memory device 136 may also include any combination of various levels of non-transitory machine-readable memory including, but not limited to, electrically erasable programmable read-only memory (EEPROM) having embedded software instructions (e.g., firmware), dynamic random-access memory (e.g., DRAM), cache, buffers, or other memory devices. In some embodiments, memory may be shared among the various processors or dedicated to particular processors.

Communication resources 138 include physical and network interface components or other suitable devices to communicate via a network 148 with one or more peripheral devices 150 (e.g., programming workstation) or one or more other devices collectively storing global variables 152 that are described later. Communication resources 138 may also include wired communication components (e.g., for coupling via a Universal Serial Bus (USB)), cellular communication components, Near Field Communication (NFC) components, Bluetooth® components (e.g., Bluetooth® Low Energy), Wi-Fi® components, and other communication components.

Instructions 154 may comprise software, a program, an application, an applet, an app, or other executable code for causing at least any of microcontroller(s) 134 to perform any one or more of the methods discussed herein. For example, instructions 154 facilitate receiving (e.g., via communication resources 138) DICOM files or similar data, as described previously. The instructions 154 then facilitate processing of the data to generate imaging biomarker for differentiating anoxic brain injury from normal controls and to potentially assess BBB integrity.

For instance, an algorithm will automatically co-register the DWI and ASL signal maps, calculate the ratio of the ASL to DWI signal or vice versa on a voxelwise basis, assign the ratio a color based on its value depending on user preference or default settings, optionally smooth the image, plot those colors on the image, and generate an image (i.e., image data) that can be viewable on PACS as part of a typical workflow. In another embodiment, an algorithm could automatically select two or more ROIs, calculate the ratio of the ASL to DWI signal or vice versa based on the obtained ROI values, and assign the status of potential anoxic/hypoxic injury based on the distribution of the calculated ratios.

Instructions 154 may reside, completely or partially, within at least one of microcontroller(s) 134 (e.g., within a processor's cache memory), memory/storage devices 136, or any suitable combination thereof. Furthermore, any portion of instructions 154 may be transferred to computing device 114 from any combination of peripheral devices 150 or the other devices storing global variables 152. Accordingly, memory of microcontroller(s) 134, memory/storage devices 136, peripheral devices 150, and the other devices are examples of computer-readable and machine-readable media.

Instructions 154 may also, for instance, comprise one or more physical or logical blocks of computer instructions, which may be organized as a routine, program, object, component, data structure, text file, or other instruction set facilitating one or more tasks or implementing particular data structures or software modules. A software module, component, or library may include any type of computer instruction or computer-executable code located within or on a non-transitory computer-readable storage medium. In certain embodiments, a particular software module, component, or programmable rule may comprise disparate instructions stored in different locations of a computer-readable storage medium, which together implement the described functionality. Indeed, a software module, component, or programmable rule may comprise a single instruction or many instructions, and may be distributed over several different code segments, among different programs, and across several computer-readable storage media. Some embodiments may be practiced in a distributed computing environment where tasks are performed by a remote processing device linked through a communications network.

Instructions 154, for example, include .Net and C libraries providing machine-readable instructions that, when executed by a processor, cause processors of the nodes to perform one or more of the aforementioned analyses, image processing, and image generation. Such processes may be performed during imaging acquisition at the MRI scanner level, although such processes could be performed at any point in the imaging pipeline.

Skilled persons will appreciate in light of this disclosure, however, that many changes may be made to the details of the above-described embodiments without departing from the underlying principles of the invention. The aforementioned techniques may provide an imagining biomarker useful in other etiologies in which the blood brain barrier physiology is altered. The scope of the present invention should, therefore, be determined only by claims and equivalents.

The invention claimed is:

1. A method for generating a diffusion to perfusion (DP) ratio brain image for determination of whether a patient has experienced an anoxic or hypoxic brain injury or other pathology that has damaged or disrupted a blood brain barrier of the patient such that a blood brain barrier anomaly is detectable, the method comprising:
receiving magnetic resonance imaging (MRI) data, the MRI data including perfusion and diffusion sequences;
calculating signal intensity ratios between co-registered locations of the perfusion and diffusion sequences by dividing first signal intensity values in one sequence by second signal intensity values at the co-registered locations in the other sequence;
generating the DP ratio brain image based on the signal intensity ratios between co-registered locations of the perfusion and diffusion sequences; and
presenting the DP ratio brain image such that the blood brain barrier anomaly is detectable by homogenous DP ratios observable from the DP ratio brain image.

2. The method of claim 1, further comprising assigning colors to the DP ratio brain image based on corresponding values of the ratios.

3. The method of claim 1, in which receiving the MRI data includes receiving a digital imaging and communications in medicine (DICOM) file.

4. The method of claim 1, in which the perfusion sequence includes an arterial spin labeling (ASL) sequence.

5. The method of claim 1, in which the diffusion sequence includes a diffusion weighted imaging (DWI) sequence.

6. The method of claim 1, further comprising co-registering the perfusion and diffusion sequences on a voxelwise basis.

7. The method of claim 1, further comprising resampling one or both the perfusion and diffusion sequences to obtain sequences having equal slice thickness.

8. The method of claim 1, further comprising applying a smoothing function to one or both perfusion and diffusion sequences.

9. The method of claim 1, further comprising applying a normalization function to one or both perfusion and diffusion sequences to allow comparison among multiple patients.

10. The method of claim 1, further comprising generating, based on the DP ratio brain image, an imaging biomarker for differentiating anoxic brain injury from normal controls.

11. The method of claim 1, further comprising generating, based on the DP ratio brain image, an imaging biomarker for evaluating physiologic and pathologic changes to permeability of the blood brain barrier.

12. A non-transitory machine-readable storage medium including instructions for generating a diffusion to perfusion (DP) ratio brain image and thereby facilitating a determination of whether a patient has experienced an anoxic or hypoxic brain injury or other pathology that has damaged or disrupted a blood brain barrier of the patient such that a blood brain barrier anomaly is detectable, the instructions, when executed by a medical imaging device, cause the medical imaging device to:
receive magnetic resonance imaging (MRI) data, the MRI data including perfusion and diffusion sequences;
calculate signal intensity ratios between co-registered locations of the perfusion and diffusion sequences by dividing first signal intensity values in one sequence by second signal intensity values at the co-registered locations in the other sequence; and
generate the DP ratio brain image based on the signal intensity ratios between co-registered locations of the perfusion and diffusion sequences; and
present the DP ratio brain image such that the blood brain barrier anomaly is detectable by homogenous DP ratios observable from the DP ratio brain image.

13. The non-transitory machine-readable storage medium of claim 12, in which the instructions further configure the medical imaging device to assign colors to the DP ratio brain image based on corresponding values of the ratios.

14. The non-transitory machine-readable storage medium of claim 12, in which the instructions further configure the medical imaging device to receive a digital imaging and communications in medicine (DICOM) file.

15. The non-transitory machine-readable storage medium of claim 12, in which the perfusion sequence includes an arterial spin label (ASL) sequence.

16. The non-transitory machine-readable storage medium of claim 12, in which the diffusion sequence includes a diffusion weighted image (DWI) sequence.

17. The non-transitory machine-readable storage medium of claim 12, in which the instructions further configure the medical imaging device to co-register the perfusion and diffusion sequences on a voxelwise basis.

18. The non-transitory machine-readable storage medium of claim 12, in which the instructions further configure the medical imaging device to resample one or both the perfusion and diffusion sequences to obtain sequences having equal slice thickness.

19. The non-transitory machine-readable storage medium of claim 12, in which the instructions further configure the medical imaging device to apply a smoothing function to one or both perfusion and diffusion sequences.

20. The non-transitory machine-readable storage medium of claim 12, in which the instructions further configure the medical imaging device to apply a normalization function to one or both perfusion and diffusion sequences to allow comparison among multiple patients.

21. The non-transitory machine-readable storage medium of claim 12, in which the instructions further configure the medical imaging device to generate, based on the DP ratio brain image, an imaging biomarker for differentiating anoxic brain injury from normal controls.

22. The non-transitory machine-readable storage medium of claim 12, wherein the instructions further configure the medical imaging device to generate, based on the DP ratio brain image, an imaging biomarker for evaluating physiologic and pathologic changes to permeability of the blood brain barrier.

23. The non-transitory machine-readable storage medium of claim 12, in which the medical imaging device is an MRI scanner.

24. The non-transitory machine-readable storage medium of claim 12, in which the medical imaging device is a picture archiving and communication system (PACS).

* * * * *